(12) United States Patent
Yamaya et al.

(10) Patent No.: US 9,342,903 B2
(45) Date of Patent: May 17, 2016

(54) METHOD FOR GENERATING IMAGE FOR PET ATTENUATION CORRECTION FROM MR IMAGE AND COMPUTER PROGRAM

(71) Applicants: NATIONAL INSTITUTE OF RADIOLOGICAL SCIENCES, Chiba-shi, Chiba (JP); SHIMADZU CORPORATION, Kyoto-shi, Kyoto (JP)

(72) Inventors: Taiga Yamaya, Chiba (JP); Takayuki Obata, Chiba (JP); Mikio Suga, Ichujawa (JP); Hiroshi Kawaguchi, Funabashi (JP); Yoshiyuki Yamakawa, Uji (JP)

(73) Assignees: NATIONAL INSTITUTE OF RADIOLOGICAL SERVICES, Chiba-shi (JP); SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 14/385,683

(22) PCT Filed: Mar. 28, 2013

(86) PCT No.: PCT/JP2013/059235
§ 371 (c)(1),
(2) Date: Sep. 16, 2014

(87) PCT Pub. No.: WO2013/147013
PCT Pub. Date: Oct. 3, 2013

(65) Prior Publication Data
US 2015/0117736 A1    Apr. 30, 2015

(30) Foreign Application Priority Data
Mar. 28, 2012 (JP) .................................. 2012-074906

(51) Int. Cl.
*G06K 9/00* (2006.01)
*G06T 11/00* (2006.01)
(Continued)

(52) U.S. Cl.
CPC ............. *G06T 11/005* (2013.01); *A61B 5/0035* (2013.01); *A61B 5/055* (2013.01);
(Continued)

(58) Field of Classification Search
CPC ...................................................... G06T 11/00
USPC ......................................................... 382/131
See application file for complete search history.

(56) References Cited

U.S. PATENT DOCUMENTS 7,010,149 B1    3/2006    Knoplioch et al.
7,983,390 B2 *  7/2011    Kitamura .................. A61B 6/00
                                                    378/155

(Continued)

FOREIGN PATENT DOCUMENTS

DE    102009027448 A1    1/2011
JP    A-63-241487         10/1988
(Continued)

OTHER PUBLICATIONS

PET and MRI: The Odd Couple or a Match Made in Heaven? Ciprian Catana, Alexander R. Guimaraes, and Bruce R. Rosen. May 2013.*

(Continued)

*Primary Examiner* — Stephen R Koziol
*Assistant Examiner* — Delomia L Gilliard
(74) *Attorney, Agent, or Firm* — Oliff PLC

(57) ABSTRACT

When an image for PET attenuation correction is generated from an MR image, the MR image captured by MRI is segmented into regions according to pixel values. In a region in which a radiation attenuation coefficient is considered to be uniform, a radiation attenuation correction value is determined by referring to an existing radiation attenuation correction value table. In a region including multiple tissues having different radiation attenuation coefficients, a radiation attenuation correction value is determined by referring to a standard image. In such a manner, an image for PET attenuation correction in which tissues having similar pixel values in the MR image but different attenuation coefficients for radiation can be distinguished and that can accommodate individual differences and an affected area such as a space occupying lesion (for example, a cancer, abscess, or the like) and an organic defect is generated.

8 Claims, 24 Drawing Sheets

(51) Int. Cl.

| | |
|---|---|
| *A61B 5/055* | (2006.01) |
| *A61B 5/00* | (2006.01) |
| *G01T 1/16* | (2006.01) |
| *A61B 6/03* | (2006.01) |
| *G01R 33/48* | (2006.01) |
| *G06T 7/00* | (2006.01) |

(52) U.S. Cl.
CPC ............ *A61B 6/037* (2013.01); *G01R 33/481* (2013.01); *G01T 1/1603* (2013.01); *G06T 7/0081* (2013.01); *A61B 2576/026* (2013.01); *G06T 2207/10088* (2013.01); *G06T 2207/10104* (2013.01); *G06T 2207/30004* (2013.01)

(56) References Cited

U.S. PATENT DOCUMENTS

| | | | | |
|---|---|---|---|---|
| 2010/0135559 | A1 | 6/2010 | Morich et al. | |
| 2011/0019895 | A1 | 1/2011 | Mizuta et al. | |
| 2011/0123083 | A1* | 5/2011 | Ojha | G01N 24/08 382/131 |
| 2011/0309251 | A1* | 12/2011 | Fenchel | A61B 6/037 250/362 |
| 2012/0155733 | A1 | 6/2012 | Wagenkenecht | |
| 2013/0101193 | A1* | 4/2013 | Ra | G06F 11/005 382/131 |
| 2013/0266198 | A1* | 10/2013 | Pereira | G06T 7/0012 382/131 |
| 2015/0065854 | A1* | 3/2015 | Ahn | A61B 6/5247 600/411 |

FOREIGN PATENT DOCUMENTS

| | | |
|---|---|---|
| JP | A-2002-542915 | 12/2002 |
| JP | A-2005-283421 | 10/2005 |
| JP | A-2006-177799 | 7/2006 |
| JP | A-2006-284346 | 10/2006 |
| JP | A-2008-22930 | 2/2008 |
| JP | A-2010-8164 | 1/2010 |
| JP | A-2010-85147 | 4/2010 |
| JP | A-2010-525857 | 7/2010 |
| WO | WO 2009/118843 A1 | 10/2009 |
| WO | 2010/032168 A2 | 3/2010 |

OTHER PUBLICATIONS

Atlas-Based Attenuation Correctino for PET/MRI. John Christian Patrick. Mar. 2013.*
Hofmann et al., "Towards quantitative PET/MRI: a review of MR-based attenuation correction techniques," *European Journal of Nuclear Medicine and Molecular Imaging*, 2009, pp. S93-S104, vol. 36.
Kops et al., "Attenuation Correction of PET Scanning Based on MRT-Images," *Nucl. Sci. Symp. & Med. Image. Conference*, 2006, pp. 241.
Kops et al., "Towards an MRI Based Attenuation Correction for Brain MR-PET," *BrainPET Conference*, 2007.
Zaidi et al., "Magnetic resonance imaging-guided attenuation and scatter corrections in three-dimensional brain positron emission tomography," *Med. Phys.*, May 2003, pp. 937-948, vol. 5.
Montandon et al., "Atlas-guided non-uniform attenuation correction in cerebral 3D PET imaging," *NeuroImage*, pp. 278-286, 2005, vol. 25.
Montandon et al., "Quantitative analysis of template-based attenuation compensation in 3D brain PET," *Computerized Medical Imaging and Graphics*, 2007, pp. 28-38, vol. 31.
Jul. 9, 2013 International Search Report issued in International Application No. PCT/JP2013/059235.
Oct. 27, 2015 Search Report issued in European Patent Application No. 13767524.5.
M. Hofmann et al.; "MRI-Based Attenuation Correction for Whole-Body PET/MRI: Quantitative Evaluation of Segmentation- and Atlas-Based Methods;" The Journal of Nuclear Medicine; vol. 52, No. 9; Sep. 2011; pp. 1392-1399.
A. Tanigawa et al.; "Hybrid segmentation-atlas method for PET-MRI attenuation correction;" 2012 IEEE Nuclear Science Symposium and Medical Imaging Conference Record (NSS/MIC); Nov. 3, 2012; pp. 2727-2729.

* cited by examiner

METHOD FOR GENERATING IMAGE FOR PET ATTENUATION CORRECTION FROM MR IMAGE AND COMPUTER PROGRAM

TECHNICAL FIELD

The present invention relates to a method for generating an image for PET attenuation correction from an MR image and a computer program, and more particularly to a method for generating an image for PET attenuation correction from an MR image by which a high-precision image for PET attenuation correction can be generated when generating an image for PET attenuation correction from an MR image, and a computer program for executing this method.

BACKGROUND ART

Inspection devices capable of observing inside the human body in a minimally invasive manner, such as X-ray CT (computed tomography) and MRI (magnetic resonance imaging), have become widely available in recent years and been contributing significantly to medical diagnosis. Such apparatuses mainly provide a morphological image obtained by visualizing a tissue structure of the living subject as a tomographic image or volume data. In contrast, nuclear medical imaging, typified by PET (positron emission tomography) and SPECT (single photon emission CT), is a device for providing a functional image obtained by quantitatively visualizing physiological information such as glucose consumption, local blood flow, oxygen consumption, and the distribution of neurotransmitter receptors. With the recent increase of diseases such as cancers, dementia, and arteriosclerotic diseases, advances are being made in its research and clinical application. PET is also attracting attention as a powerful technique for promoting molecular imaging research for imaging the behavior of biomolecules.

PET/CT simultaneously capable of PET and X-ray CT imaging has recently been developed and become widespread in the clinical field. This has made possible diagnosis in light of both biological functions and body tissue. For example, in the diagnosis of cancer by PET, only the tumor portion is output with a high intensity. It may therefore be difficult to determine in which organ the tumor is. The superposition with X-ray CT, which provides excellent viewability of the form of the organs, is thus useful.

Instead of the combination with X-ray CT, PET/MRI to carry out diagnosis in combination with MRI has recently attracted attention. MRI not only can visualize the inside of living body with high spatial resolution, but also has the characteristics that the contrast of soft tissue is better than with X-ray CT, and that a functional image such as hemodynamic imaging and metabolic product concentration measurement by MR spectroscopy can be acquired. PET/MRI also has a lot of advantages, including that it is possible to avoid radiation exposure which is a problem with PET/CT. Its implementation is thus much expected (see Non-Patent Literature 1).

A PET device obtains information from annihilation radiations emitted from a radioactive drug reaching detectors. PET image reconstruction uses the detection data of annihilation radiations emitted in 180° directions. The annihilation radiations undergo attenuation while passing through various tissues of the body to reach the detectors. As a result, quantitative performance is greatly disturbed in deep portions of the subject. To obtain a quantitative drug distribution, the attenuation of the annihilation radiations needs to be corrected. A spatial distribution of radiation attenuation coefficient (μ-map) needed for attenuation correction in the conventional PET image reconstruction is created on the basis of transmission measurement (referred to as transmission scan) separate from the data acquisition of the PET. The transmission scan is performed by rotating a radiation source 12 around the subject 10 and performing detection with a detector 14 as illustrated in FIG. 1 (see Patent Literatures 1 to 3). In the case of PET/CT, attenuation correction is usually performed by converting the X-ray CT image into a μ-map without the foregoing transmission scan.

MRI collects intensities obtained from protons (hydrogen nuclei) in tissues, and therefore cannot directly obtain the radiation attenuation rate of the respective tissues. Since the current design concept of PET/MRI does not include a transmission source similar to that of X-ray CT, a method for generating a μ-map as an alternative to the transmission scan is needed.

As a method for generating a μ-map by using an MR image, a segmentation method (see Non-Patent Literatures 2, 3, and 4) and a standard image reference method (see Non-Patent Literatures 5 and 6) have been proposed so far. In the segmentation method, as illustrated in FIG. 2, an MR image m is segmented into regions such as a high intensity region (soft tissue), a medium intensity region (water), and a low intensity region (air and bone) tissue by tissue, and μ values inherent to the tissues are substituted to generate a μ-map. In the standard image reference method, as illustrated in FIG. 3, a standard image (standard MR image $m_s$ or standard μ-map $μ_s$) is deformed to the MR image m of the patient by using affine transformation or the like.

CITATION LIST

Patent Literatures

Patent Literature 1: Japanese Patent Application Laid-Open No. 2005-283421
Patent Literature 2: Japanese Patent Application Laid-Open No. 2006-284346
Patent Literature 3: Japanese Patent Application Laid-Open No. 2008-22930

Non-Patent Literatures

Non-Patent Literature 1: Bernd Pichler, Bernhard Scholkopf and Thomas Beyer Matthias Hofmann, "Towards quantitative PET/MRI: a review of MR-based attenuation correction techniques," EUROPEAN JOURNAL OF NUCLEAR MEDICINE AND MOLECULAR IMAGING, vol. 36 (Supplement 1), pp. 93-104, March 2009.
Non-Patent Literature 2: E. Rota Kops, P. Qin, M. Mueller-Veggian, and H. Herzog, "Attenuation Correction of PET Scanning Based on MRT-Images," Nucl. Sci. Symp. & Med. Imag. Conference, 241 2006.
Non-Patent Literature 3: E. Rota Kops and H. Herzog, "Towards an MRI based attenuation correction for brain MR-PET,"2007 BrainPET Conference, May 2007.
Non-Patent Literature 4: H. Zaidi, M.-L. Montandon, and D. O. Slosman, "Magnetic resonance imaging-guided attenuation and scatter corrections in three dimensional brain positron emission tomography," Med. Phys., vol. 30, pp. 937-948, 2003.
Non-Patent Literature 5: Marie-Louise Montandon and Habib Zaidi, "Atlas-guided non-uniform attenuation correction in cerebral 3D PET imaging," Neuroimage, vol. 25, no. 1, pp. 278-286, March 2005.

Non-Patent Literature 6: Marie-Louise Montandon and Habib Zaidi, "Quantitative analysis of template-based attenuation compensation in 3D brain PET," Computerized Medical Imaging and Graphics, vol. 31, pp. 28-38, January 2007.

SUMMARY OF THE INVENTION

Problem to be Solved by the Invention

However, as illustrated in FIG. 2, the former segmentation method has the problem that tissues having very different μ values (in the case of the example, bone and air) are both low intensities in the MR image and are therefore indistinguishable. Blood, which has a μ value equivalent to that of soft tissue, may also be indistinguishable from air and bone.

On the other hand, the latter standard image reference method has, as illustrated in FIG. 3, the problem of being unable to accommodate individual differences or an affected area such as a space occupying lesion (a cancer, abscess, etc.) and an organic defect.

The present invention has been achieved in order to solve the foregoing conventional problems. It is an object of the present invention to generate an image for PET attenuation correction in which tissues having very different μ values can be distinguished and that can accommodate individual differences and an affected area such as a space occupying lesion (a cancer, abscess, etc.) and an organic defect.

Means for Solving the Problem

The present invention solves the foregoing problems by, when generating an image for PET attenuation correction from an MR image, segmenting an MR image captured by MRI into regions according to pixel values, determining a radiation attenuation correction value in a region in which a radiation attenuation coefficient is considered to be uniform by referring to an existing radiation attenuation correction value table, and determining a radiation attenuation correction value in a region including multiple tissues having different radiation attenuation coefficients by referring to a standard image.

Here, the standard image may be deformed to an MR image of a subject when the standard image is referred to.

The standard image may be referred to by using an image of whole body tissue or an image of some tissues of the body tissue.

The standard image may be an image for PET attenuation correction, a CT image, or a UTE image. As employed herein, a UTE image refers to an image that can be generated on the basis of an MRI image captured with an ultrashort echo time (Ultra short TE) and in which bone shows a high intensity value.

The MR image and the standard image may be adjusted to each other in resolution.

At least either one of the radiation attenuation correction value table and the standard image may be modified according to personal information about the subject (DNA, age, sex, height, weight, place of birth, place of residence, and/or medical history).

The subject's own radiation attenuation correction values or the image for PET attenuation correction, or the CT image or the UTE image may be repeatedly used as at least either one of the radiation attenuation correction value table and the standard image.

The present invention also provides a computer program for making a computer execute any of the methods described above.

Effect of the Invention

According to the present invention, in a region in which differences in the radiation attenuation correction value (also referred to as μ value) can be distinguished by referring to the pixel values of the MR image, μ values inherent to the tissues are substituted by the segmentation method. In a region in which a distinction cannot be made by using the pixel values of the MR image (for example, a low intensity region including bone and air), μ values are determined by referring to the standard image by the standard image reference method. Accurate μ values can thus be assigned to the region in which a distinction cannot be made by using the pixel values of the MR image, while individual differences and an affected area such as a brain defect portion can be accommodated.

MODE FOR CARRYING OUT THE INVENTION

Hereinafter, embodiments of the present invention will be described in detail with reference to the drawings.

Figure 4:
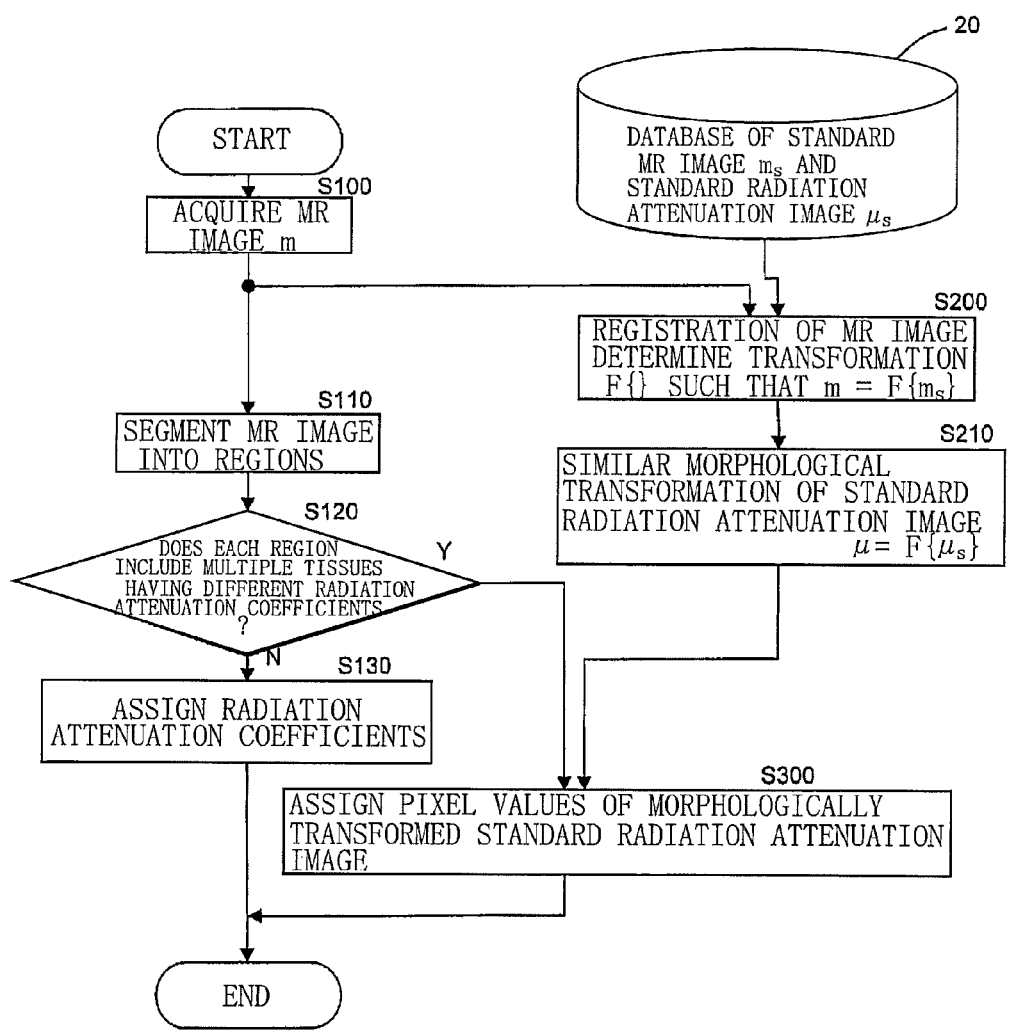
FIG. 4 is a flowchart showing a processing procedure according to a first embodiment of the present invention.

A first embodiment of the present invention is implemented by a procedure shown in FIG. 4.

Specifically, in step S100, an MR image m is initially acquired as with the conventional segmentation method.

Figure 5:
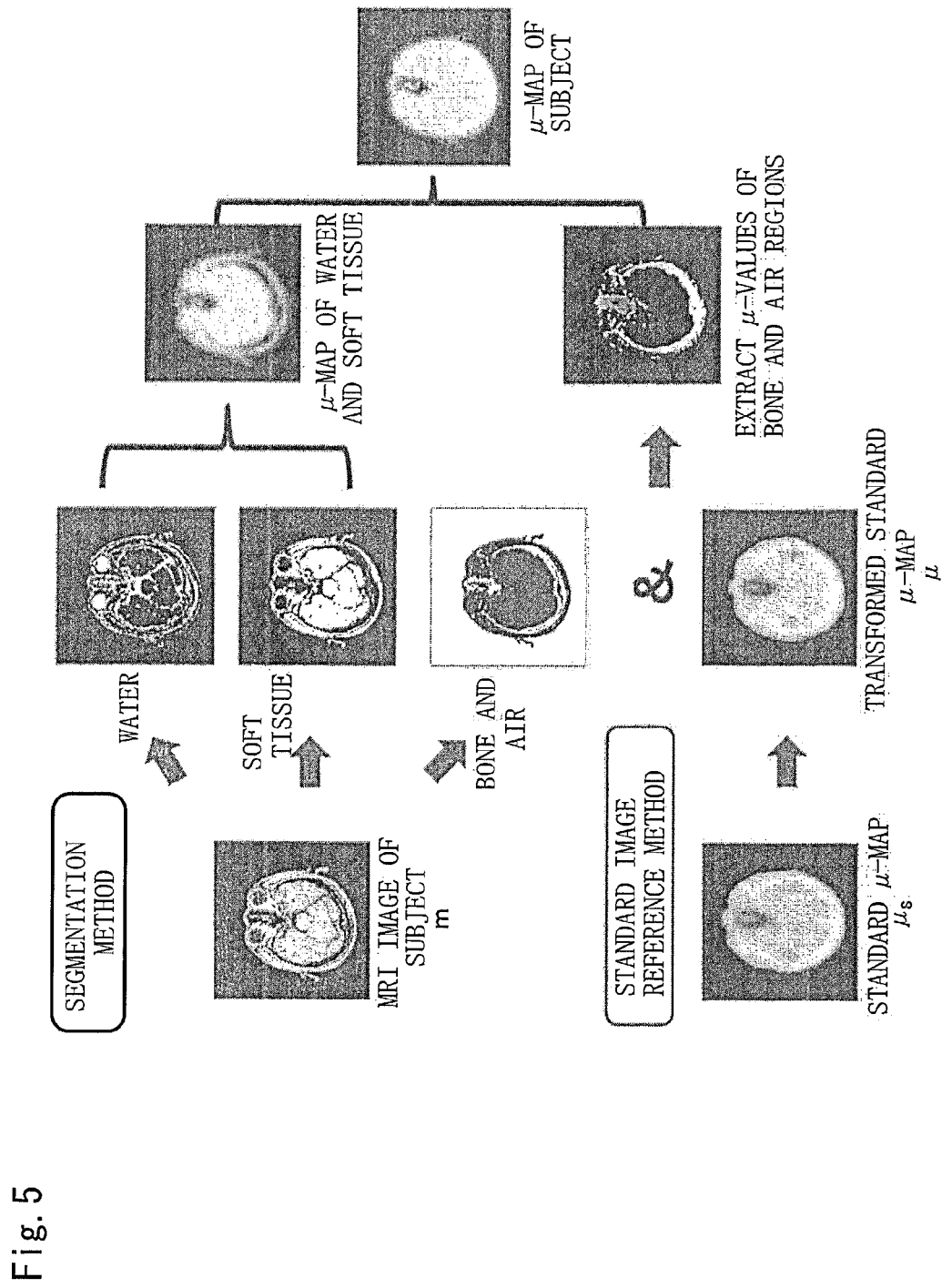
FIG. 5 is a diagram showing examples of images of the first embodiment.

Next, in step S110, as illustrated in FIG. 5, the MR image is divided into, for example, high intensity regions corresponding to soft tissue, medium intensity regions corresponding to water, and low intensity regions corresponding to air and bone on the basis of the pixel values of the MR image.

Next, in step S120, whether each intensity region includes multiple tissues having different radiation attenuation coefficients is determined. If the determination result is negative and the intensity region is determined to be a high intensity region corresponding to soft tissue or a medium intensity region corresponding to water, the radiation attenuation coefficient of soft tissue (for example, $\mu$=0.095) is assigned to the high intensity region, and the radiation attenuation coefficient of water (for example, $\mu$=0.097) to the medium intensity region.

Figure 1:
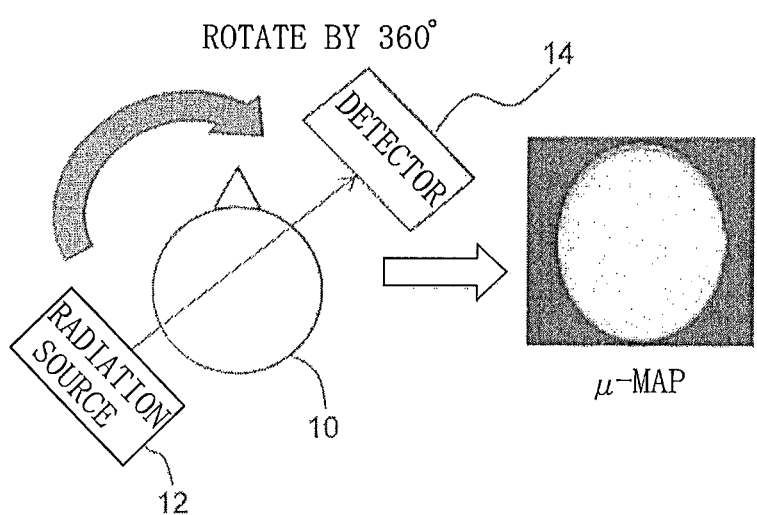
FIG. 1 is a diagram showing an outline of a conventional transmission method.
Figure 2:
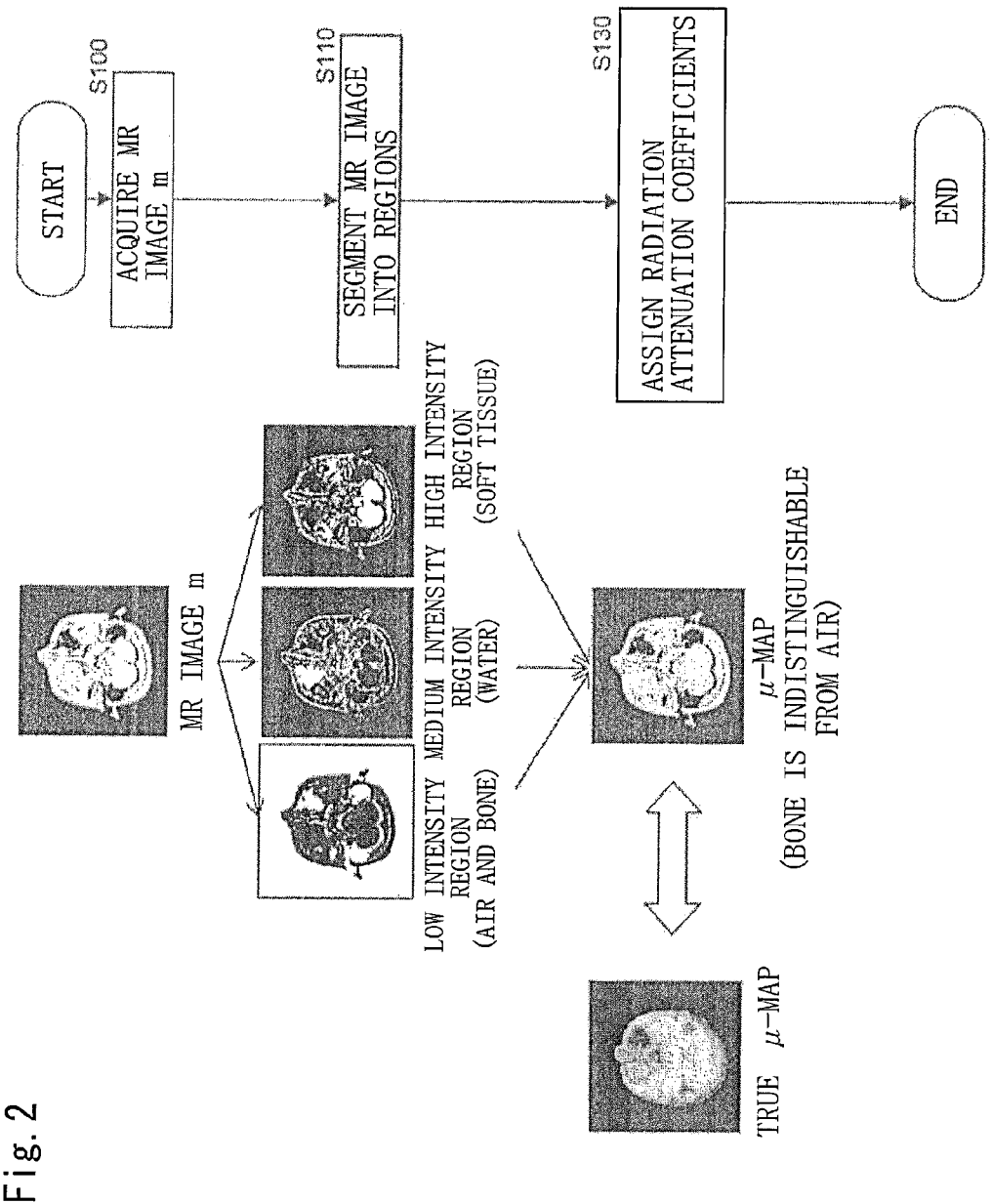
FIG. 2 is a diagram showing a conventional segmentation method.
Figure 3:
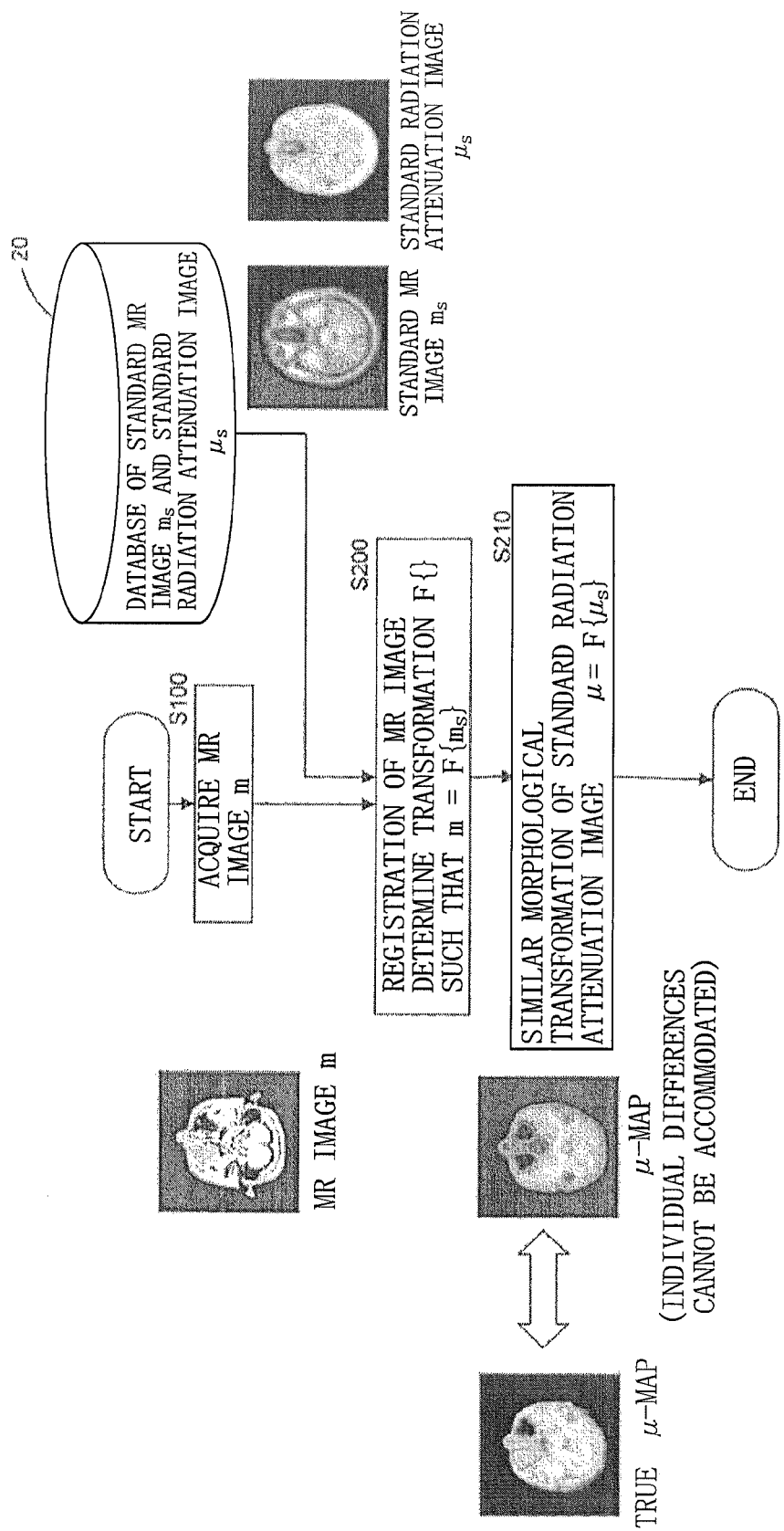
FIG. 3 is a diagram showing a conventional standard image reference method.

Meanwhile, in step S200, transformation F{ } such that m=F{$m_s$} for registration of the MR image m acquired in step S100 is determined by using a database 20 of a standard MR image 1% and a standard radiation attenuation image $\mu_s$ as with the conventional standard image reference method shown in FIG. 3.

Next, in step S210, morphological transformation $\mu$=F{$\mu_s$} of the standard radiation attenuation image is similarly performed.

If the determination result of step S120 is positive and the intensity region is determined to be a region including multiple tissues having different radiation attenuation coefficients, for example, a low intensity region in which air is indistinguishable from bone, the processing proceeds to step S300. The pixel values of the standard radiation attenuation image $\mu_s$ morphologically transformed in step S210 are assigned to the low intensity region, whereby different radiation attenuation coefficients are assigned to air and bone.

Figure 6:
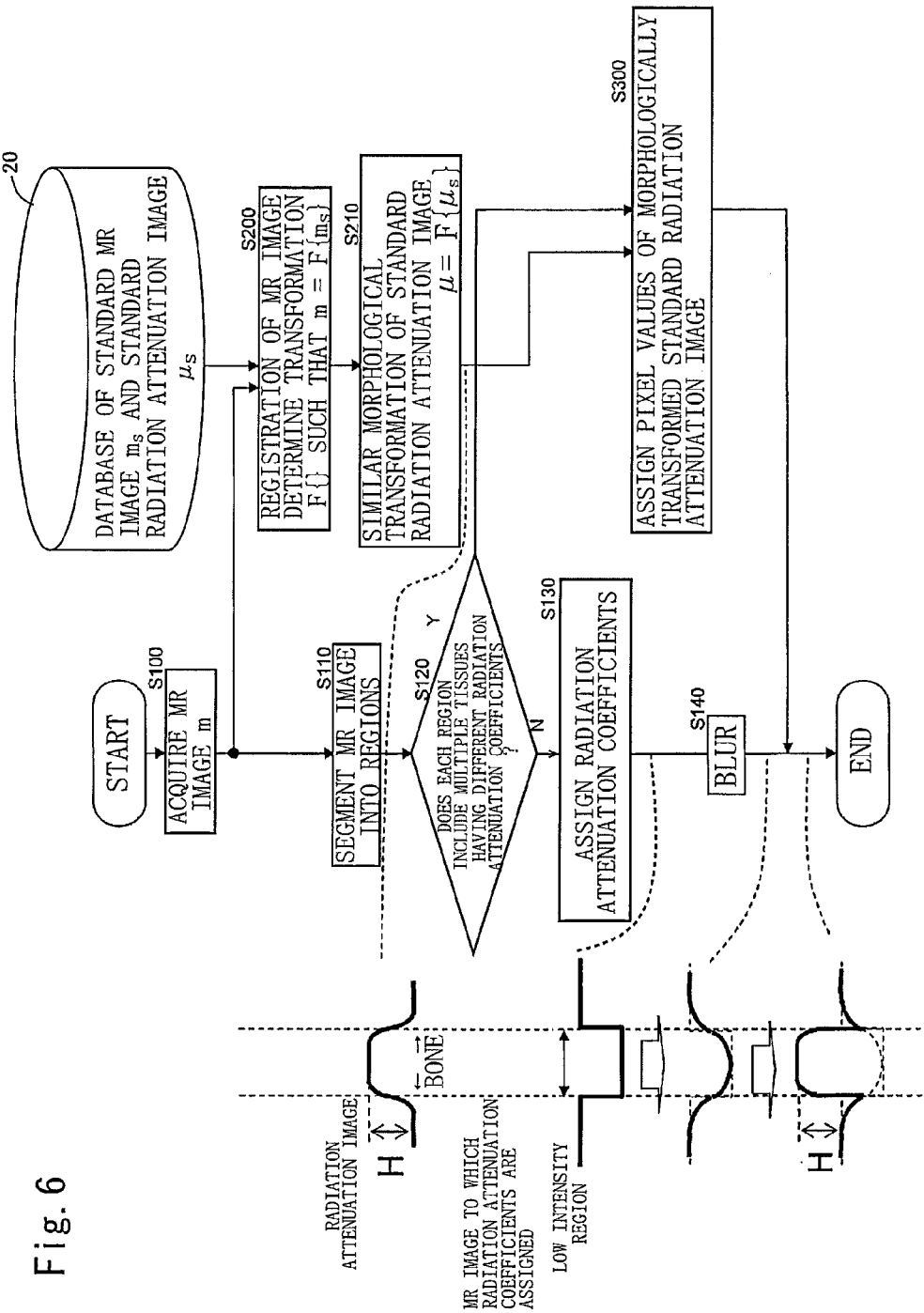
FIG. 6 is a flowchart showing a processing procedure according to a second embodiment of the present invention.

Note that the MR image and the radiation attenuation image acquired in the first embodiment have different resolutions, and may become less viewable if simply combined. FIG. 6 shows a second embodiment in which such a problem is solved.

In the present embodiment, in the process of similar processing to that of the first embodiment, the MR image having high resolution is blurred to have resolution equivalent to that of the radiation attenuation image in step S140. The blurring of step S140 can be used immediately after step S130 and before the final application of the $\mu$ values of the standard image.

According to the present embodiment, the result (radiation attenuation image) of step S130 and the standard image (MR image) are equalized in resolution, so that an accurate image can be displayed. However, if the original MR image and the radiation attenuation image have a large difference in resolution, the application of strong blurring may lower the radiation attenuation coefficients near bone regions as shown in the schematic diagram of FIG. 6.

Figure 7:
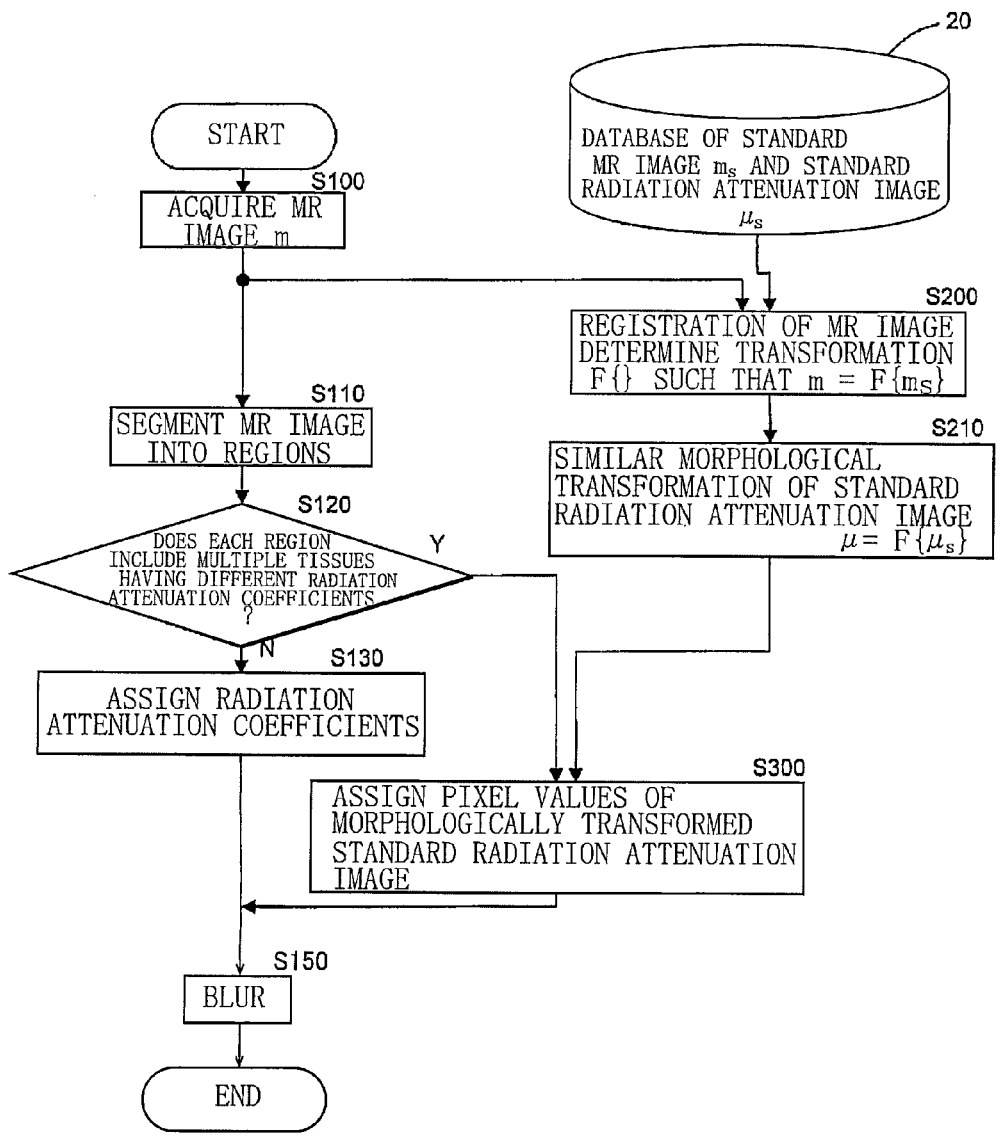
FIG. 7 is a flowchart showing a processing procedure according to a third embodiment of the present invention.

It should be appreciated that the method for blurring is not limited to the second embodiment. As in a third embodiment shown in FIG. 7, blurring may be applied in step S150 immediately before the end.

According to the present embodiment, the resolution can be adjusted to that of the PET detector, whereby the measurement can be brought close to actual radiation attenuation coefficients. The blurring can be omitted to reduce man-hours and lower the calculation cost.

Figure 8:
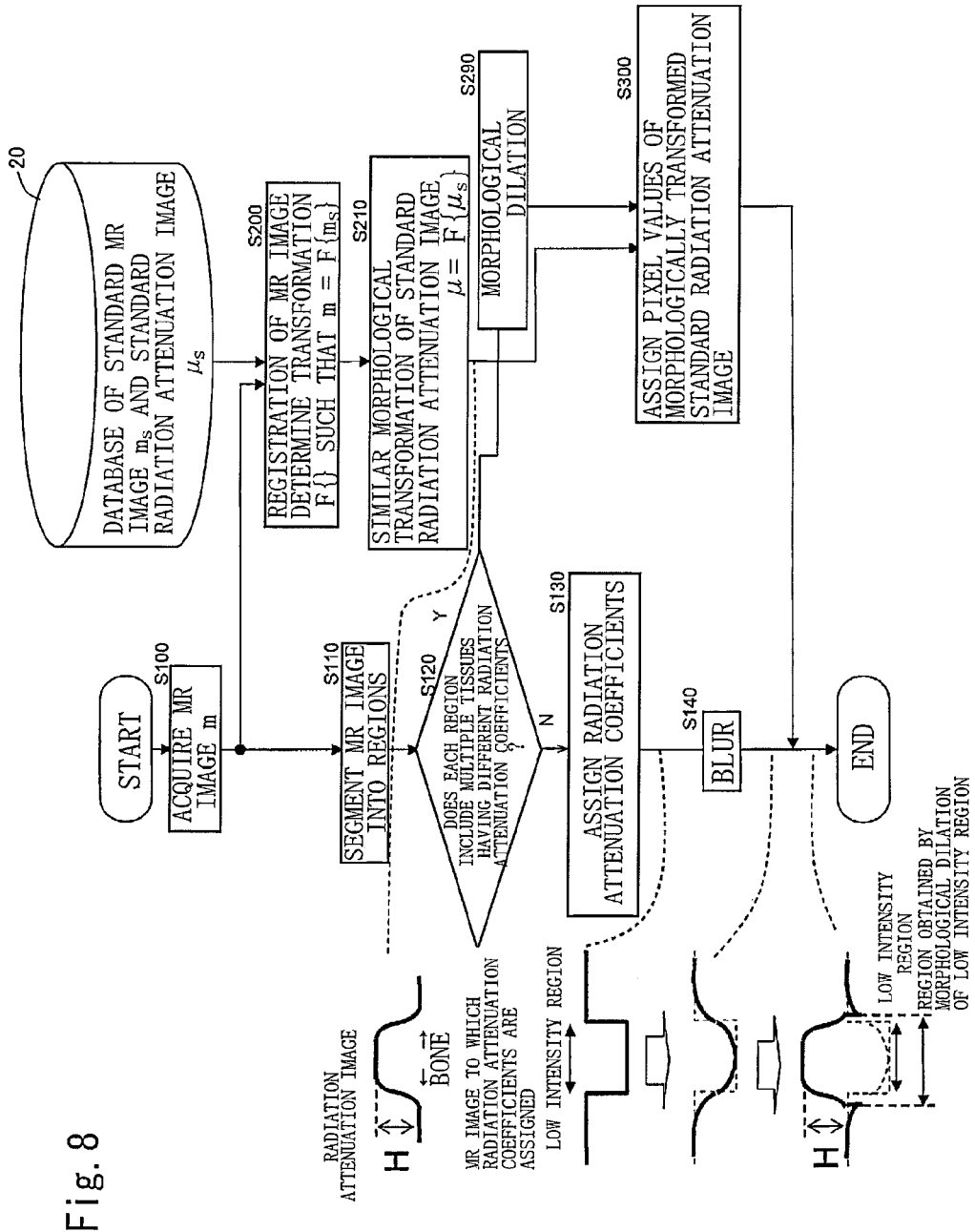
FIG. 8 is a flowchart showing a processing procedure according to a fourth embodiment of the present invention.

Next, FIG. 8 shows a fourth embodiment of the present invention in which a difference in resolution is absorbed by a different method.

In the present embodiment, in similar processing to that of the second embodiment shown in FIG. 6, if the determination result of step S120 is positive, the low intensity region is expanded in step S290. Then, in step S300, the pixel values of the morphologically transformed standard radiation attenuation image are assigned.

According to the present embodiment, a drop in the radiation attenuation coefficients near bone regions can be suppressed to connect the radiation attenuation image and the MR image more smoothly.

Even in the present embodiment, like the third embodiment, blurring may be applied immediately before the end.

Figure 9:
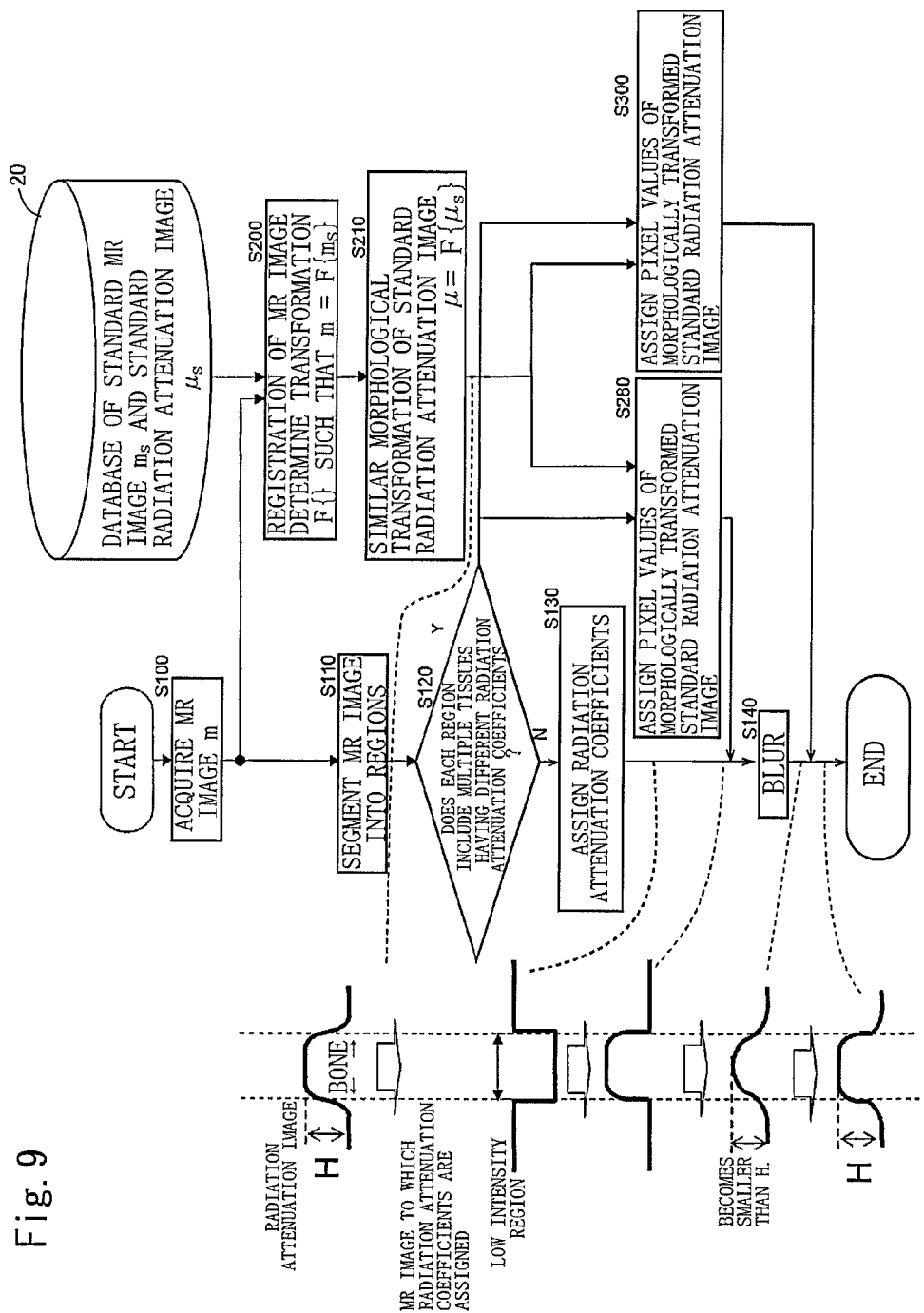
FIG. 9 is a flowchart showing a processing procedure according to a fifth embodiment of the present invention.

Next, FIG. 9 shows a fifth embodiment of the present invention in which a difference in resolution is absorbed by yet another method.

In the present embodiment, in similar processing to that of the second embodiment shown in FIG. 6, the pixel values of the morphologically transformed standard radiation attenuation image are assigned in steps S280 and S300 before and after the blurring of step S140.

According to the present embodiment, a drop in the radiation attenuation coefficient near bone regions may be able to be further suppressed while maintaining the radiation attenuation coefficient (the height H of the image) of bone.

The effect of the methods according to the second to fifth embodiments depends on the degree of the difference in resolution between the original MR image and the radiation attenuation image. The amount of blurring in step S140 and the amount of morphological dilation in S290 of the fourth embodiment therefore need to be adjusted.

Figure 10:
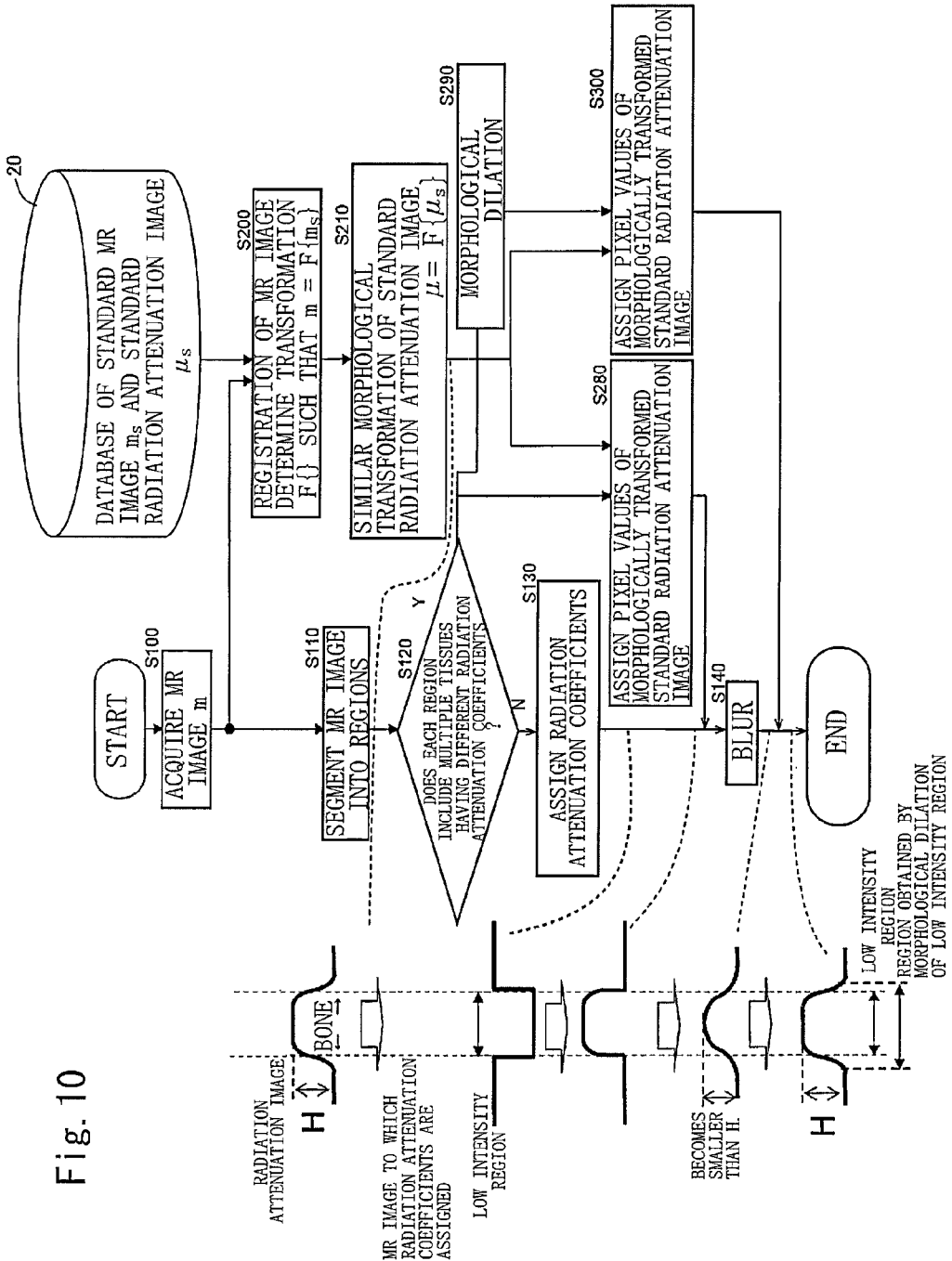
FIG. 10 is a flowchart showing a processing procedure according to a sixth embodiment of the present invention.

Next, FIG. 10 shows a sixth embodiment of the present invention in which a difference in resolution is absorbed by yet another method.

In the present embodiment, in similar processing to that of the fifth embodiment shown in FIG. 9, the same morphological dilation S290 as that of the fourth embodiment shown in FIG. 8 is performed at the time of assignment after the blurring processing S140. As compared to the methods of the second to fifth embodiments, the method of the sixth embodiment can stably correct the difference in resolution between the MR image and the radiation attenuation image.

Figure 11:
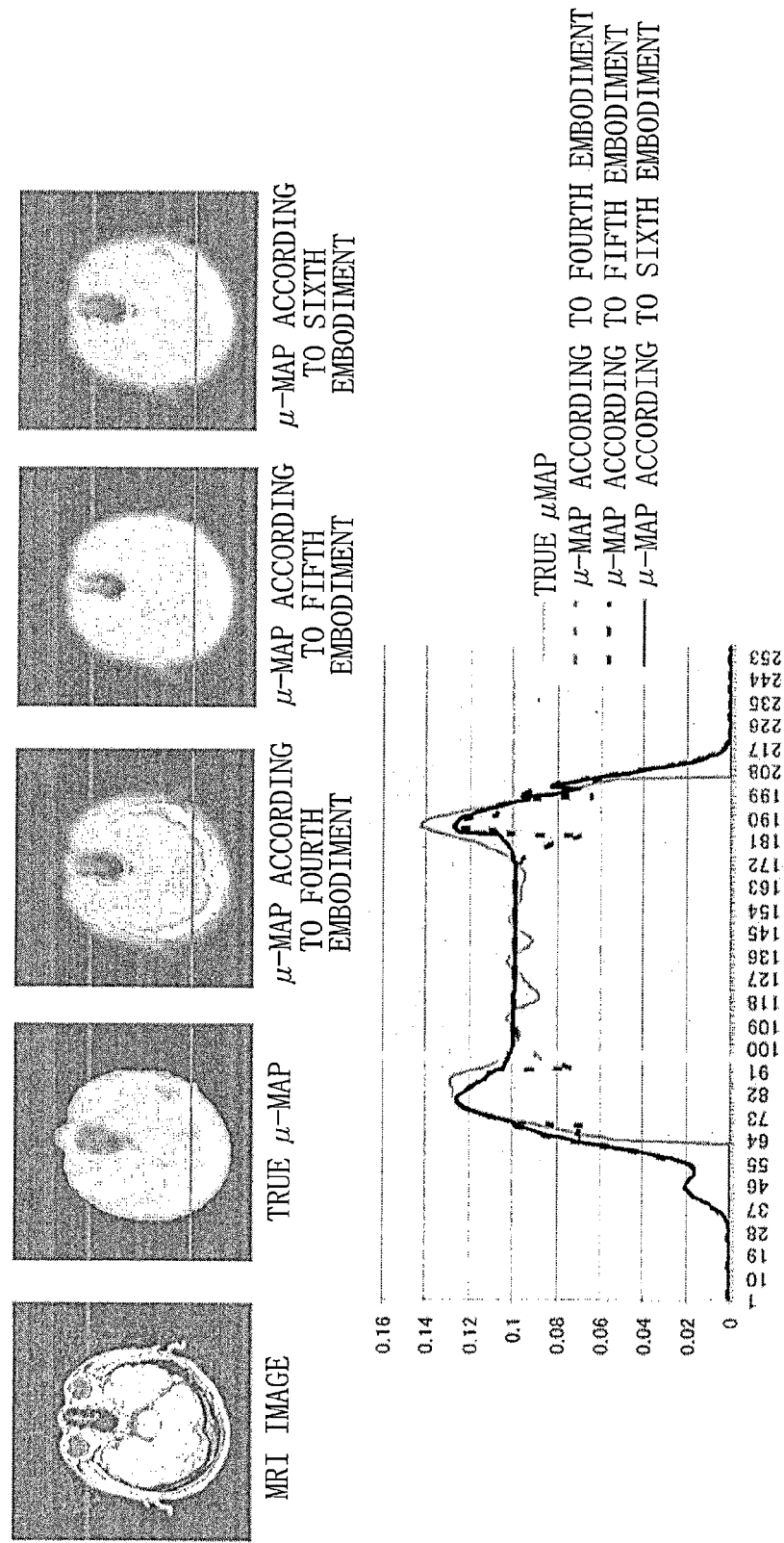
FIG. 11 is a diagram showing examples of μ-maps where a difference in resolution is taken into account by the fourth to sixth embodiments in a comparative manner.

FIG. 11 shows an MRI image, a true $\mu$-map, and the processing results of the fourth to sixth embodiments in a comparative manner.

Figure 12:
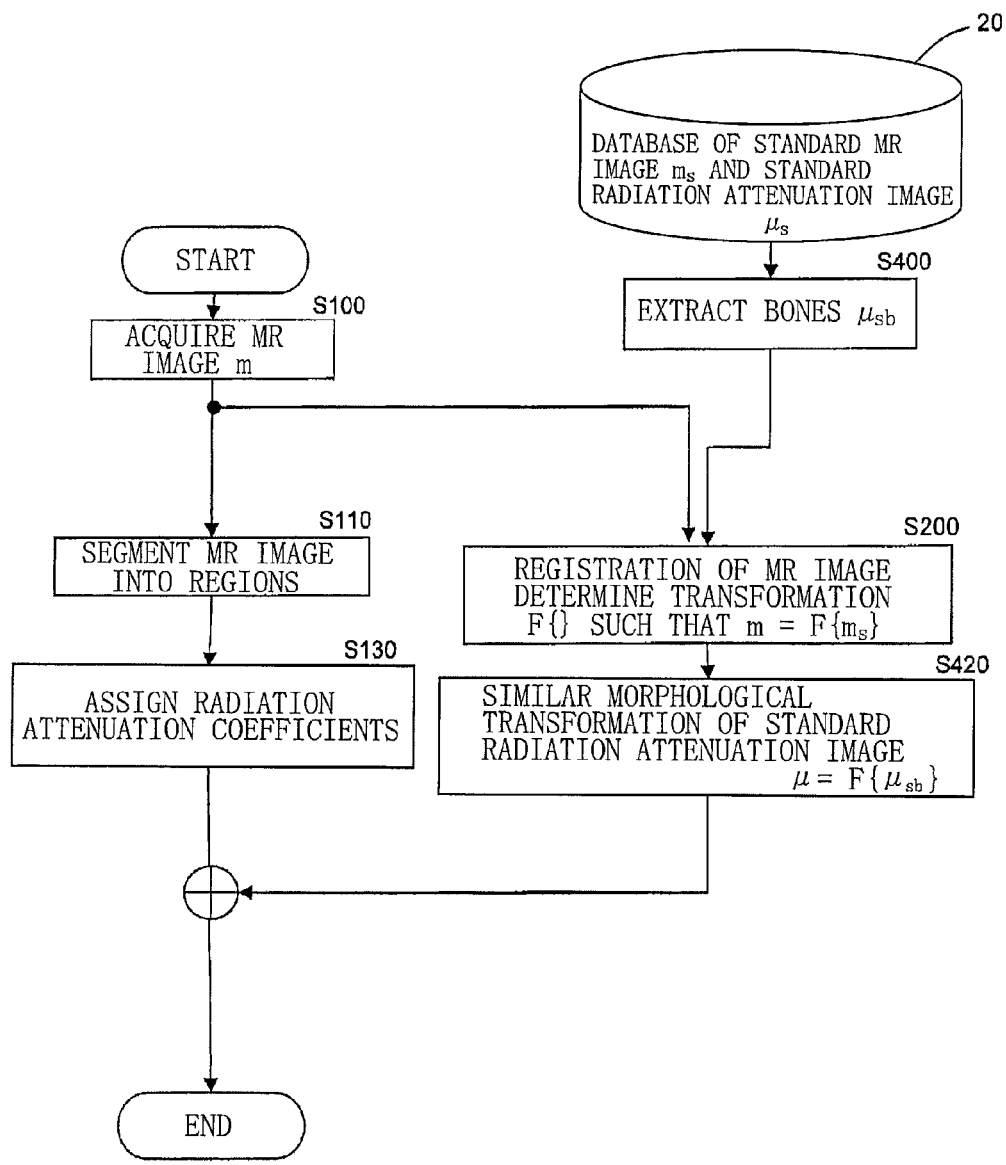
FIG. 12 is a flowchart showing a processing procedure according to a seventh embodiment of the present invention.

In any of the foregoing embodiments, the morphological transformation of the radiation attenuation image is performed after the registration of the MR images and the standard radiation attenuation image. FIG. 12 shows a seventh embodiment of the present invention in which bones are extracted first, and morphological transformation is performed on such portions.

In the present embodiment, in step S400, bone portions $\mu_{sb}$ are initially extracted from the database 20 of the standard MR image $m_s$ and the standard radiation attenuation image $\mu_s$.

Next, in the same step S200 as that of the first embodiment, transformation F{ } such that m=F{$m_s$} is determined to perform registration of the MR images.

Next, in step S420, the morphology of the radiation attenuation image is transformed with respect to the bone portions extracted in step S400, and is combined with the radiation attenuation coefficients determined in step S130.

In the present embodiment, bone portions are extracted first, and the morphological transformation is performed only on the bone portions. This eliminates the need for the determination of step S120, and results in high precision.

In any of the foregoing embodiments, the database 20 of the standard radiation attenuation image $\mu_s$ is used. As in an eighth embodiment shown in FIG. 13, a database 30 of a standard CT image $c_s$ may be used instead.

In the present embodiment, in the same step S200 as that of the first embodiment, transformation F{ } such that m=F{$m_s$} is determined to perform registration to the MR image m obtained in step S100.

Next, in step S520, morphological transformation c=F{$c_s$} of the standard CT image is similarly determined.

Next, in step S530, transformation from the CT image $c_s$ to the radiation attenuation image $\mu$ is determined.

Then, if the determination result of step S120 is positive, the pixel values of the morphologically transformed standard radiation attenuation image are assigned to, for example, a low intensity region in step S300.

According to the present embodiment, the radiation attenuation coefficients can be assigned by using the CT image which has a smaller difference in resolution from the MR image. Despite being a CT image, the standard image is subject to a drop in resolution due to averaging processing. The processing for absorbing a difference in resolution like the third to sixth embodiments is thus effective.

Figure 14:
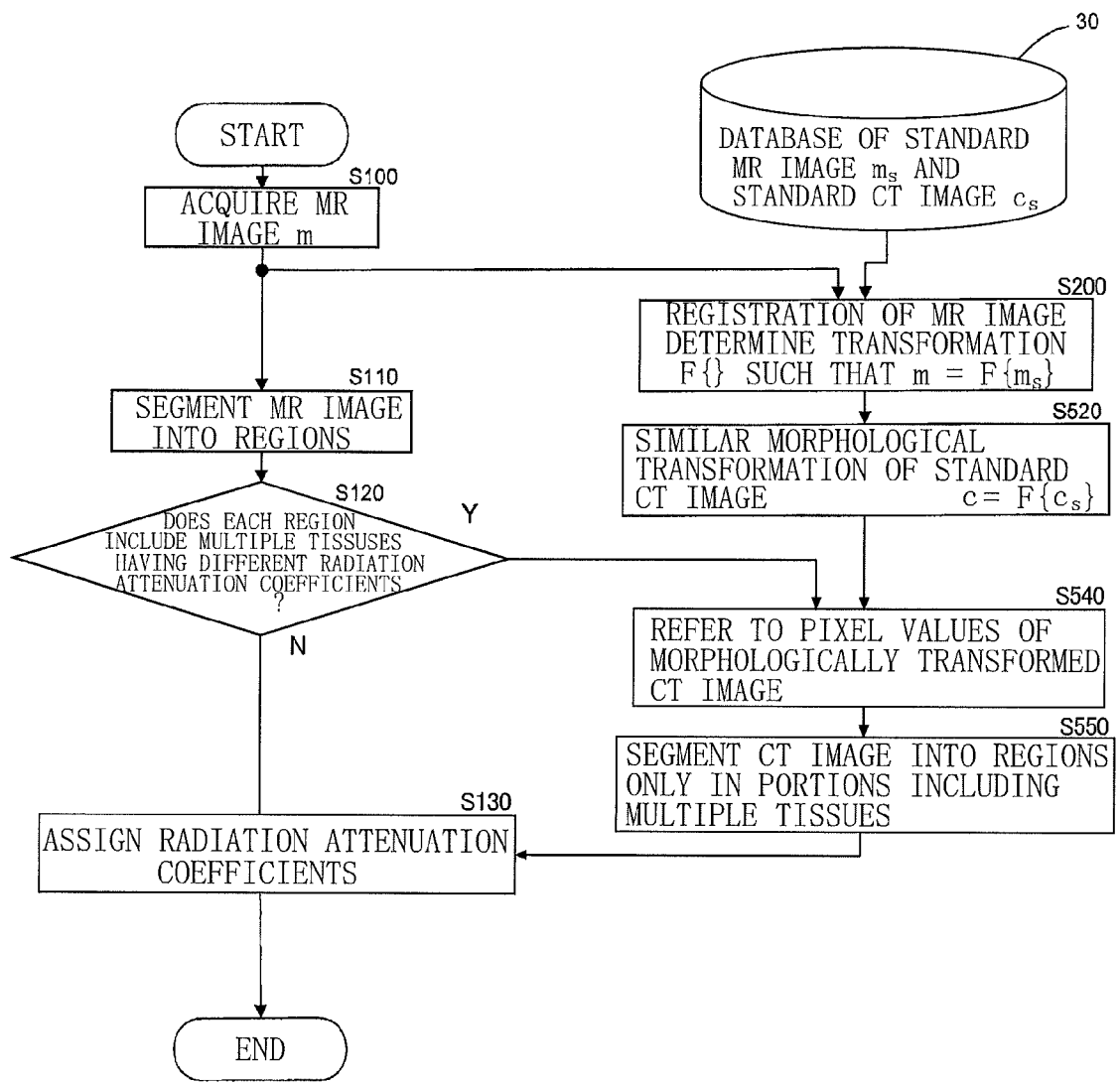
FIG. 14 is a flowchart showing a processing procedure according to a ninth embodiment of the present invention.

Next, FIG. 14 shows a ninth embodiment of the present invention which similarly uses a CT image.

Figure 13:
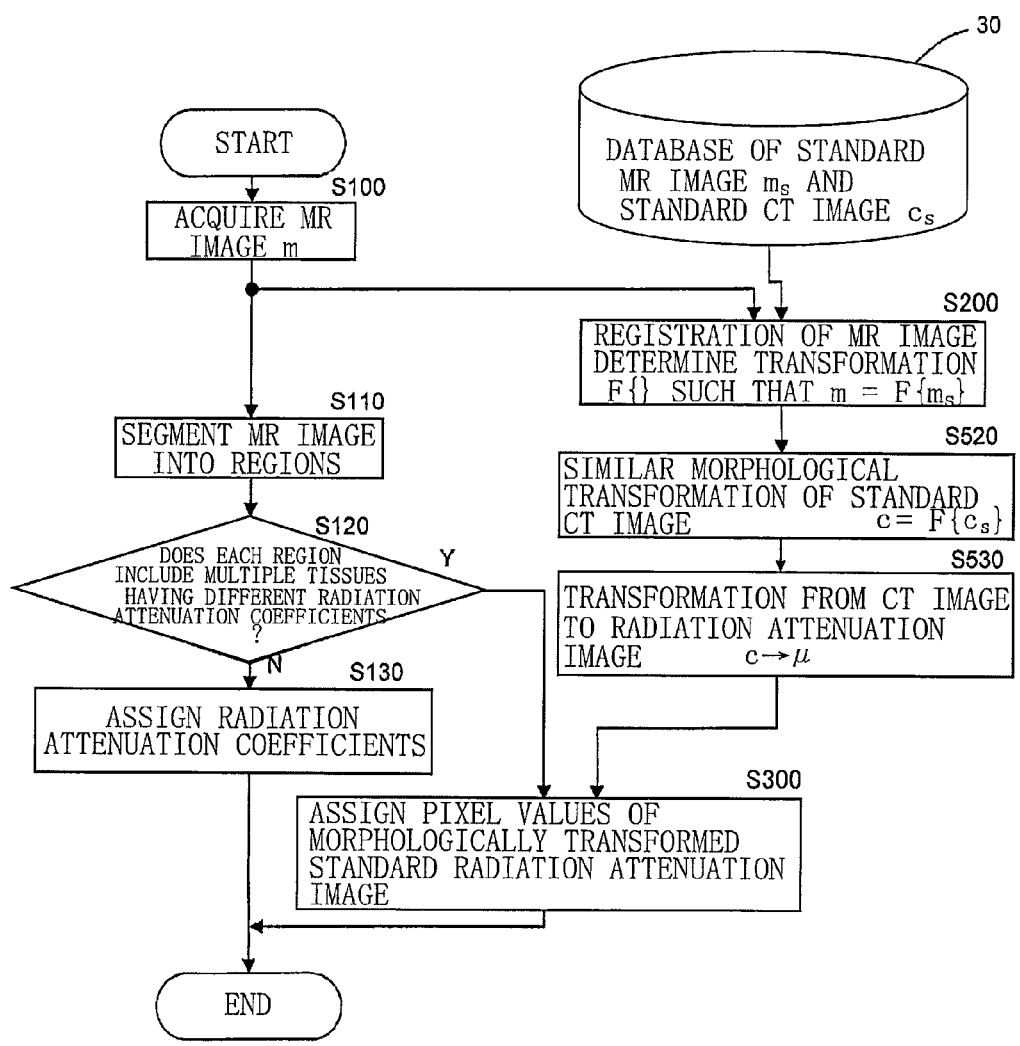
FIG. 13 is a flowchart showing a processing procedure according to an eighth embodiment of the present invention.

In the present embodiment, in a processing procedure similar to that of the eighth embodiment shown in FIG. 13, the pixel values of the morphologically transformed CT image are referred to in step S540 with respect to the regions determined to include multiple tissues having different radiation attenuation coefficients in step S120. In step S550, the CT image is segmented into regions only in the portions including the multiple tissues. Then, in step S130, the radiation attenuation coefficients of the tissues for radiation are assigned.

Figure 15:
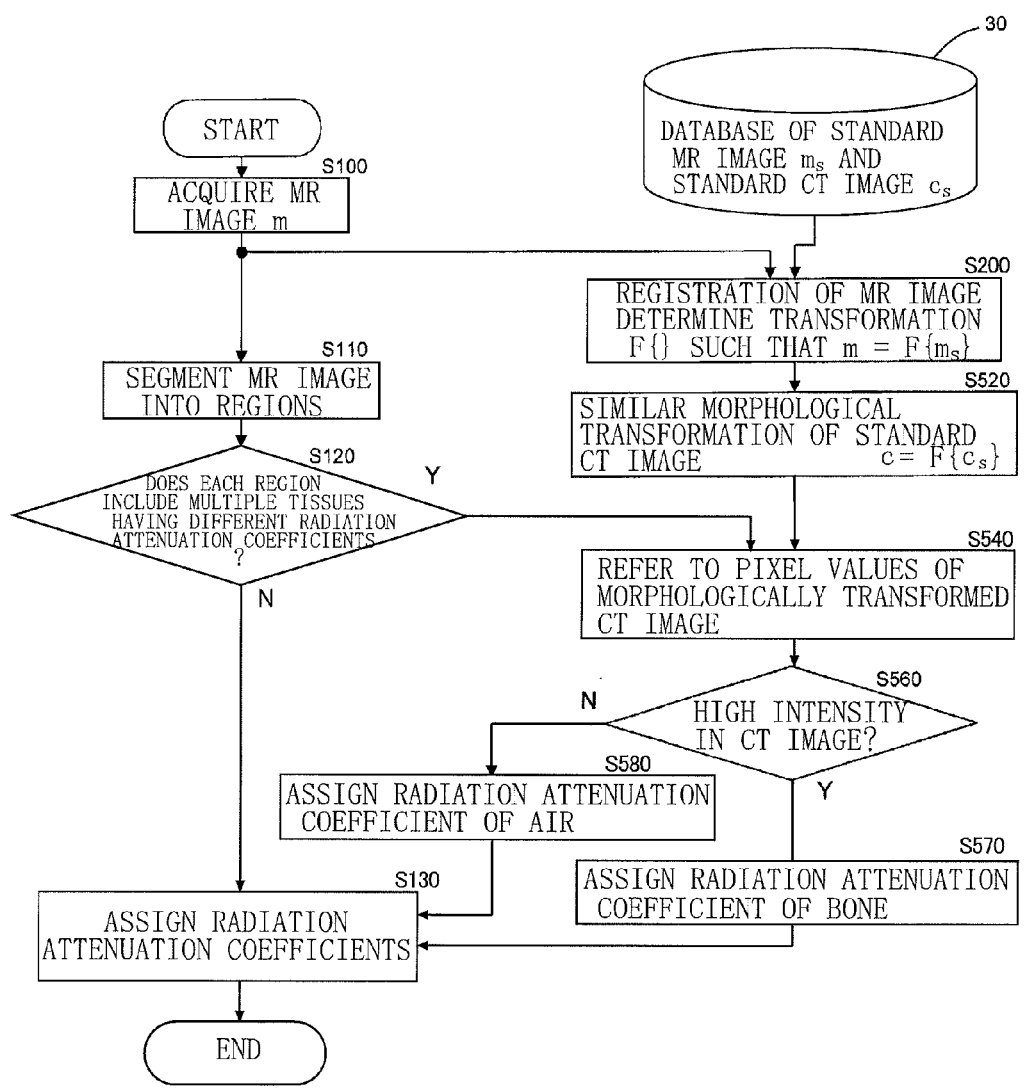
FIG. 15 is a flowchart showing a processing procedure according to a tenth embodiment of the present invention.

Specifically, as in a tenth embodiment shown in FIG. 15, after the end of step S540, the processing proceeds to step S560 to determine whether the region is a high intensity in the CT image. If the determination result is positive and the region is determined to be a bone region, the processing proceeds to step S570 to assign the radiation attenuation coefficient of bone.

On the other hand, if the determination result of step S560 is negative and the region is determined to be an air region, the processing proceeds to step S580 to assign the radiation attenuation coefficient of air.

Figure 16:
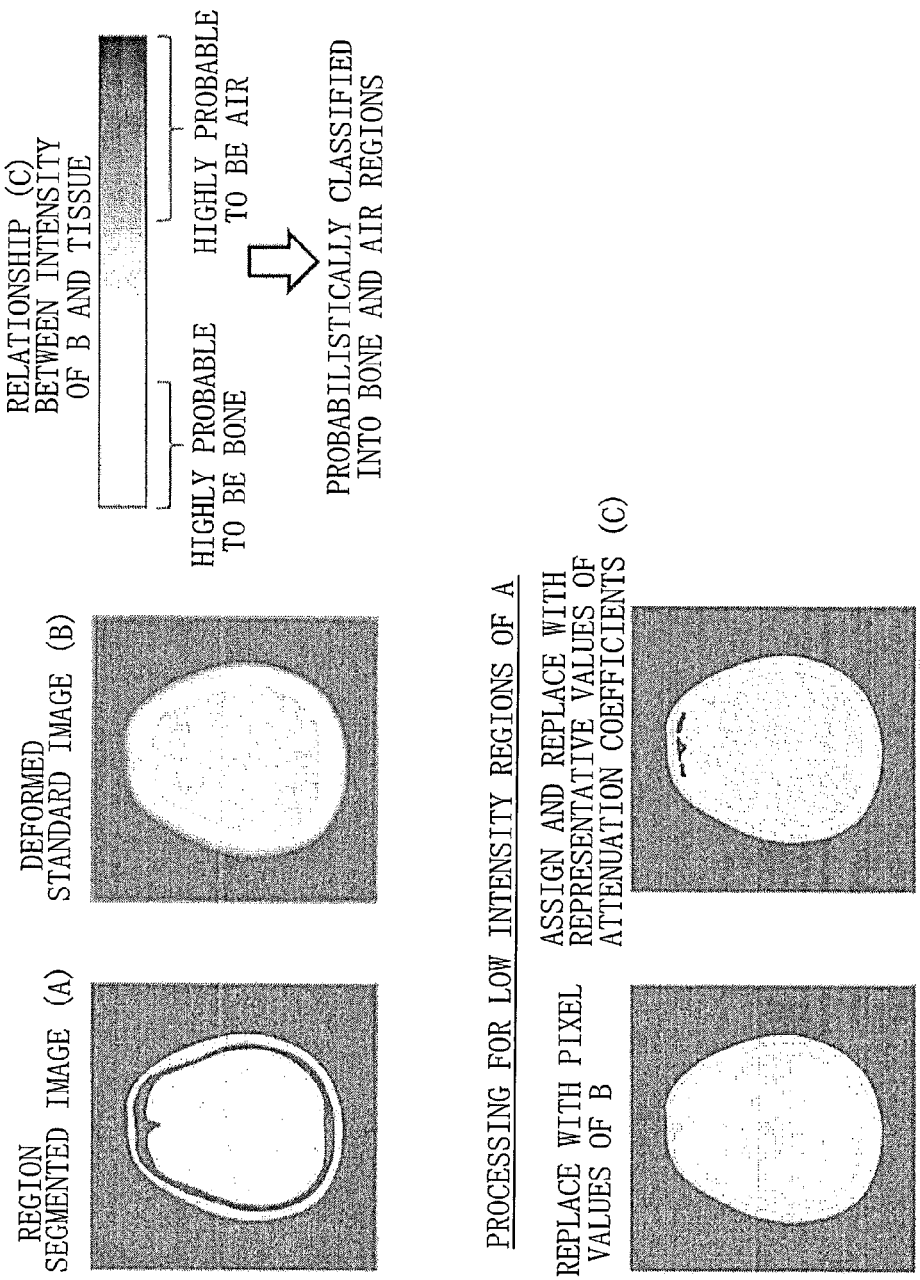
FIG. 16 is a diagram showing how to classify regions into bone and air regions according to the tenth embodiment.

In the present embodiment, as illustrated in FIG. 16, bone and air are distinguished by using the CT image. This enables highly accurate assignment.

Figure 17:
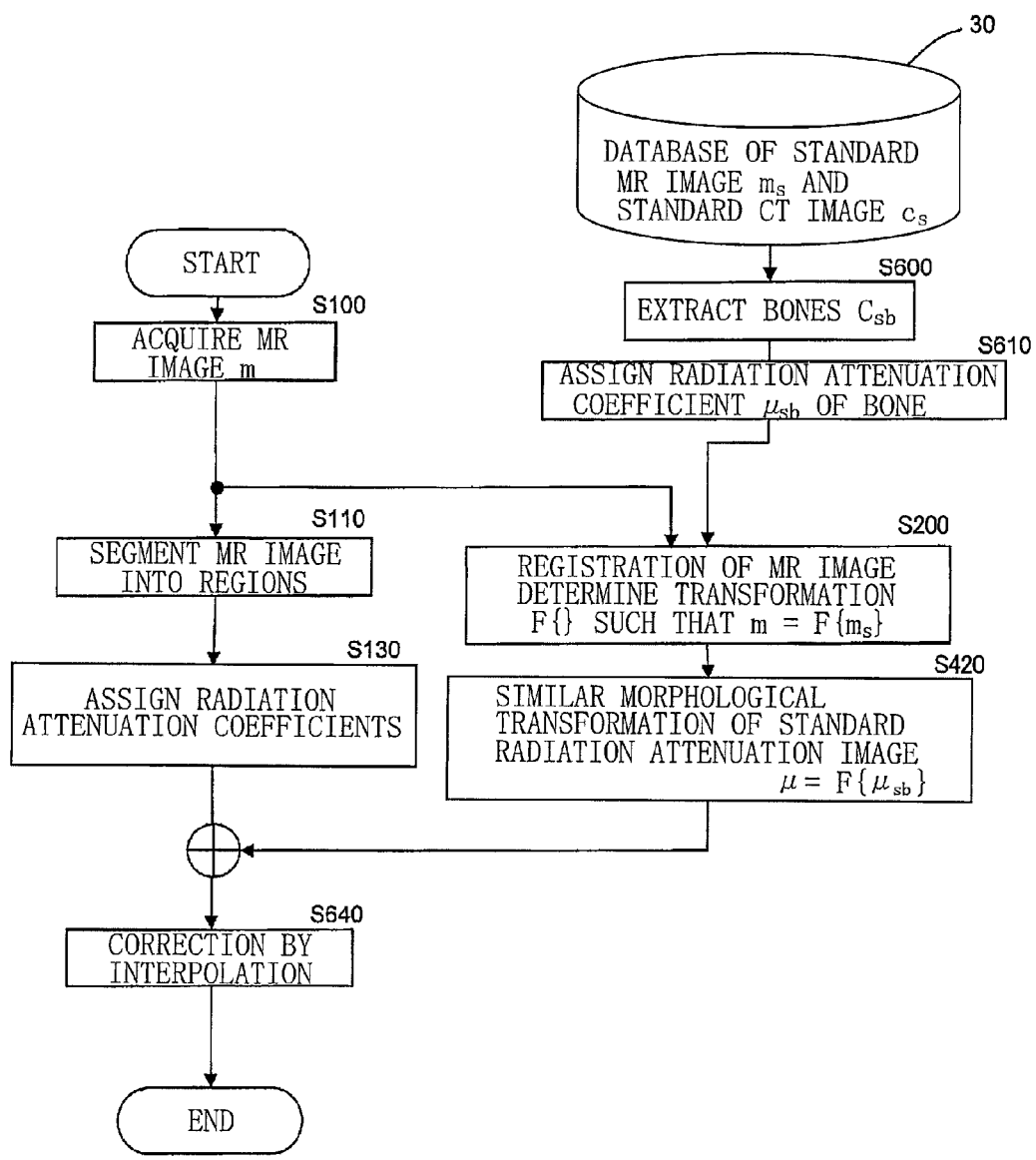
FIG. 17 is a flowchart showing a processing procedure according to an eleventh embodiment of the present invention.

Next, FIG. 17 shows an eleventh embodiment of the present invention which similarly uses a CT image to extract bones.

The present embodiment includes processing similar to that of the seventh embodiment shown in FIG. 12. In step S600, bones $c_{sb}$ are extracted from the database 30 of the standard MR image $m_s$ and the standard CT image cs. Next, in step S610, the radiation attenuation coefficient $\mu_{sb}$ of bone is assigned. Next, in step S200, the MR image is registered. In step S420, the morphological transformation of the standard radiation attenuation image is performed.

Note that if the estimation by the transformation F{ } is imperfect and some gaps or overlaps occur, then in step S640, correction processing may be performed by morphological dilation and erosion and/or nearest neighbor interpolation according to need.

Figure 18:
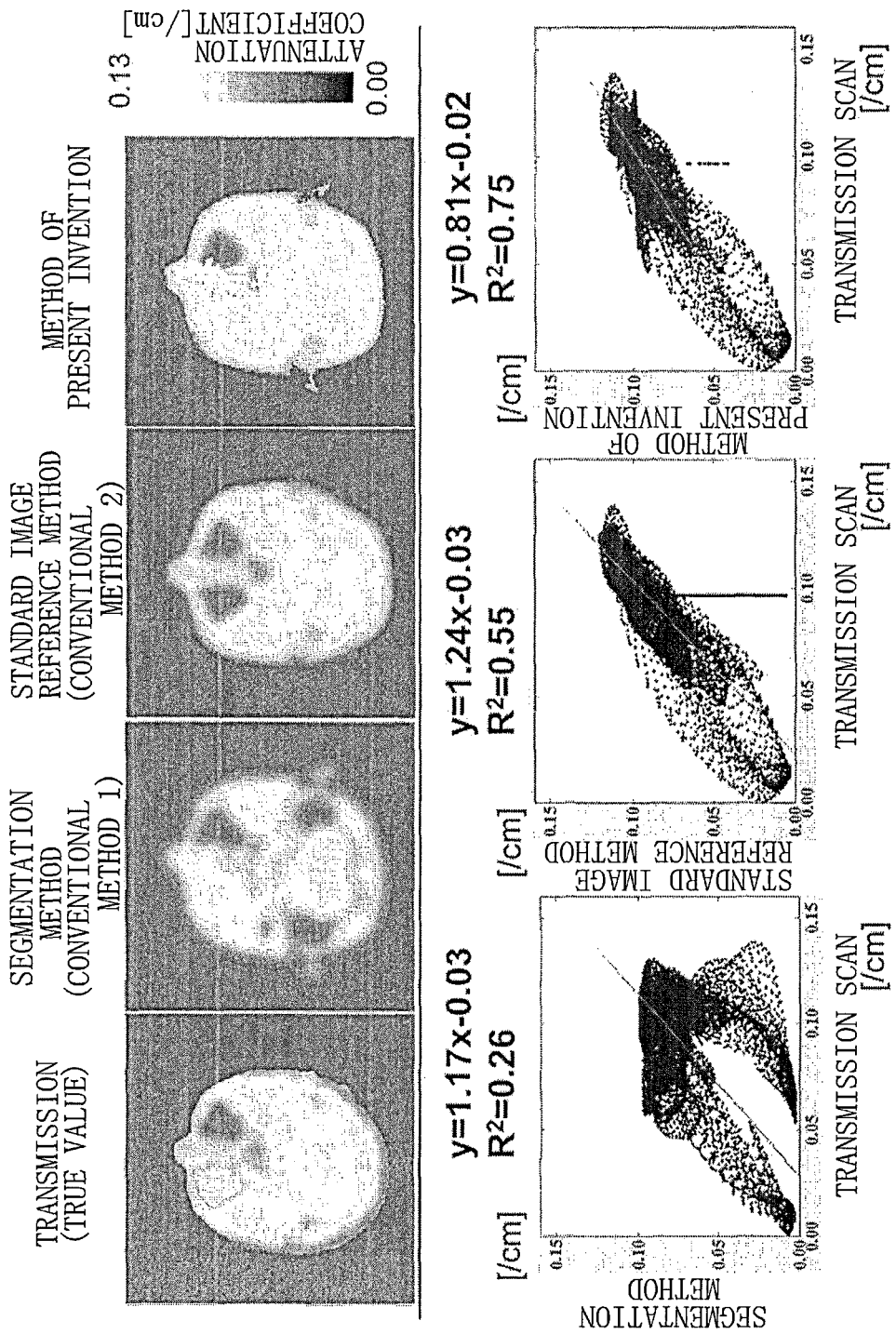
FIG. 18 is a diagram showing processing results of pseudo sinusitis by the conventional methods and the method of the present invention.

FIG. 18 shows the processing results of an image of a subject with pseudo sinusitis by the conventional methods and the method of the present invention in a comparative manner.

It is clear that the method of the present invention provides better correlation than the segmentation method and the standard image reference method.

Figure 19:
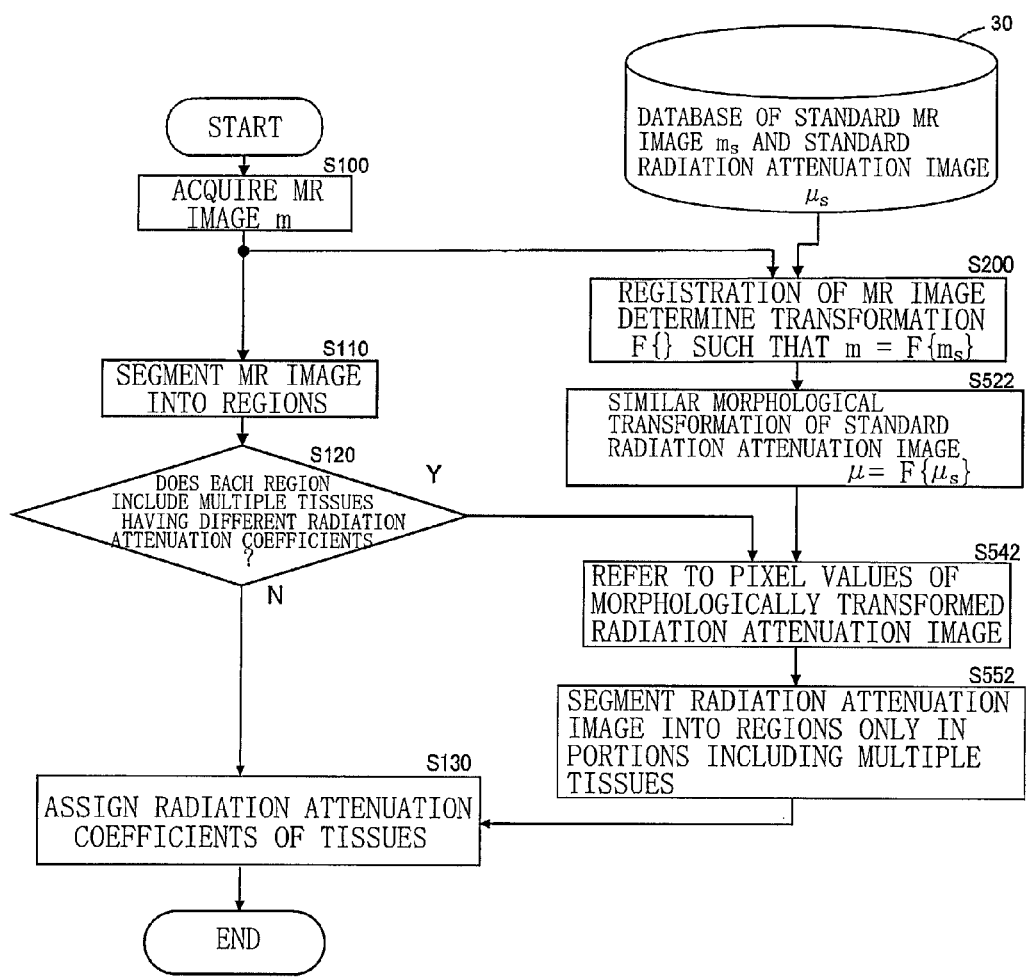
FIG. 19 is a flowchart showing a processing procedure according to a twelfth embodiment of the present invention.

FIG. 19 shows a twelfth embodiment in which the standard radiation attenuation image is used instead of the standard CT image in the ninth embodiment shown in FIG. 14. Differences from the ninth embodiment consist in that a database 30 of the standard MR image and the standard radiation attenuation image is used as the database, and that in steps S522, S542, and S552, the standard radiation attenuation image is used instead of the standard CT image. In other respects, the present embodiment is the same as the ninth embodiment. A description thereof is thus omitted.

Next, embodiments using a standard UTE image instead of the standard radiation attenuation image or the standard CT image will be described.

Figure 20:
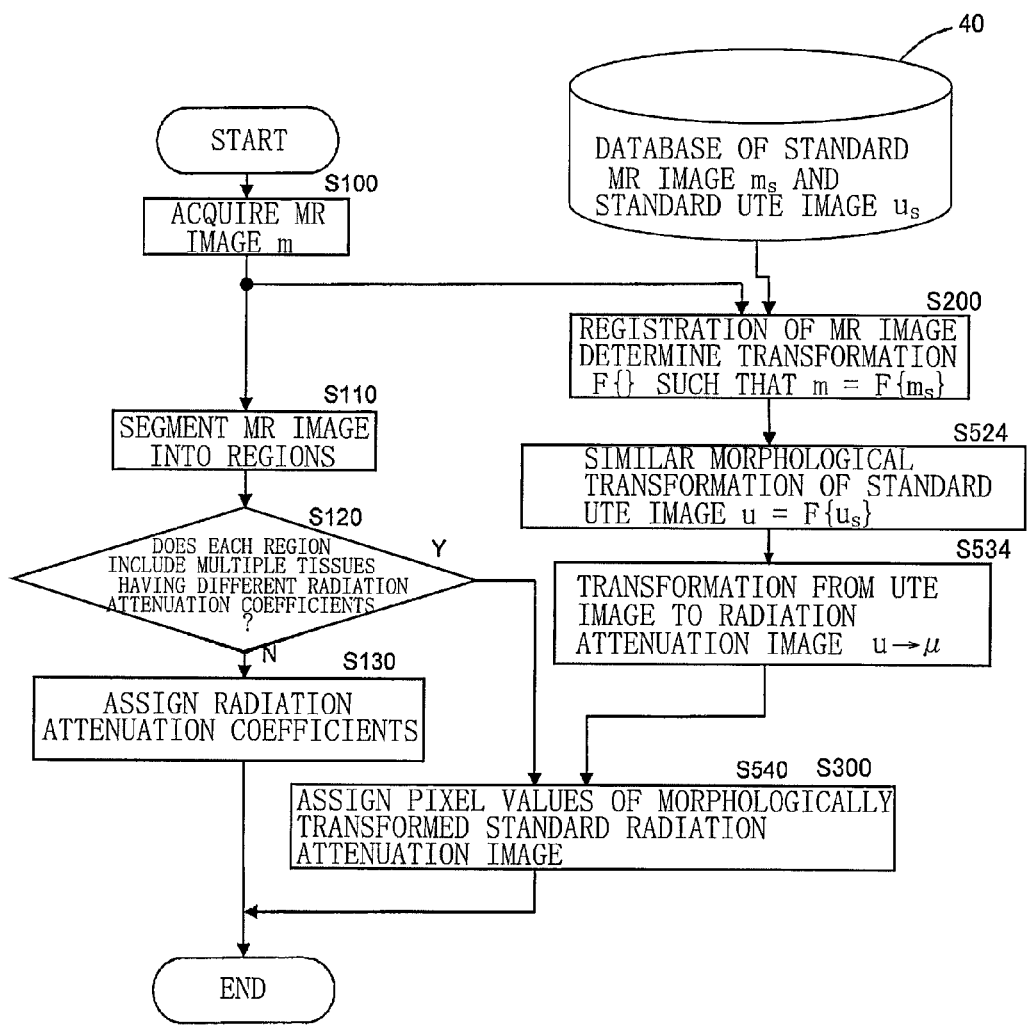
FIG. 20 is a flowchart showing a processing procedure according to a thirteenth embodiment of the present invention.

FIG. 20 shows a thirteenth embodiment in which the standard UTE image is used instead of the standard CT image in the eighth embodiment shown in FIG. 13. Differences from the eighth embodiment consist in that a database 40 of the standard MR image and the standard UTE image is used as the database, and that in steps S524 and S534, the standard UTE image is used instead of the standard CT image. In other respects, the present embodiment is the same as the eighth embodiment. A description thereof is thus omitted.

Figure 21:
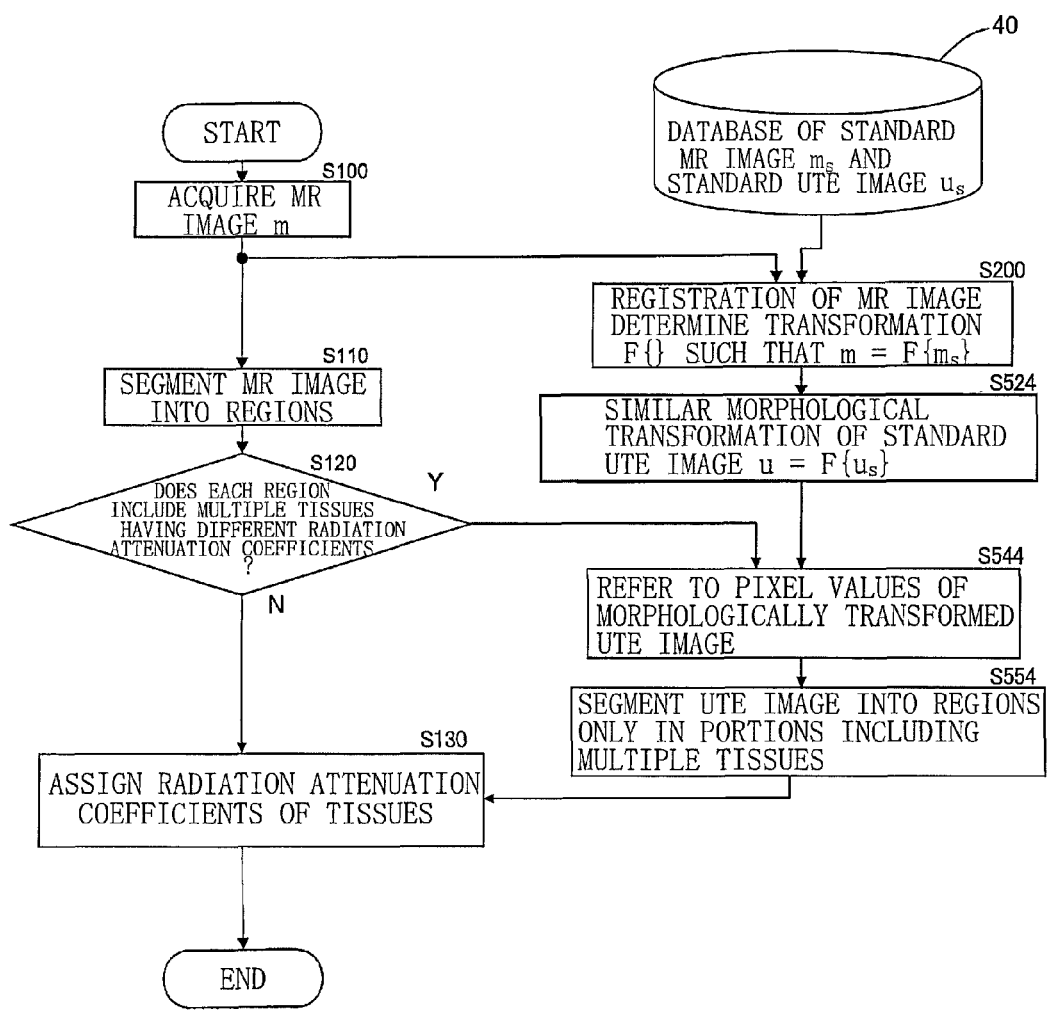
FIG. 21 is a flowchart showing a processing procedure according to a fourteenth embodiment of the present invention.

FIG. 21 shows a fourteenth embodiment in which the standard UTE image is used instead of the standard CT image in the ninth embodiment shown in FIG. 14. Differences from the ninth embodiment consist in that the database 40 of the standard MR image and the standard UTE image is used as the database, and that in steps S524, S544, and S554, the standard UTE image is used instead of the standard CT image. In other respects, the present embodiment is the same as the ninth embodiment. A description thereof is thus omitted.

Figure 22:
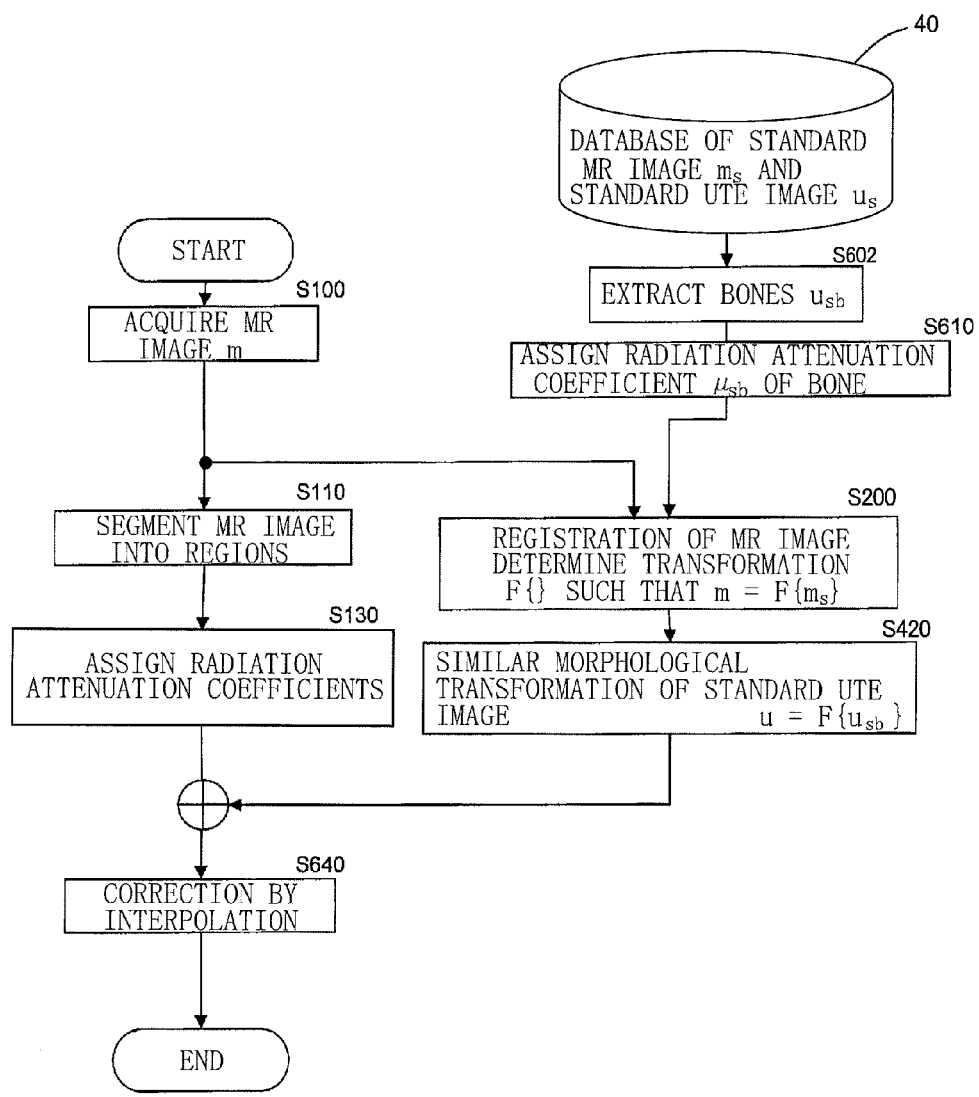
FIG. 22 is a flowchart showing a processing procedure according to a fifteenth embodiment of the present invention.

FIG. 22 shows a fifteenth embodiment in which the standard UTE image is used instead of the standard CT image in the eleventh embodiment shown in FIG. 17. A difference from the eleventh embodiment consists in that the database 40 of the standard MR image and the standard UTE image is used as the database. In other respects, the present embodiment is the same as the eleventh embodiment. A description thereof is thus omitted.

Figure 23:
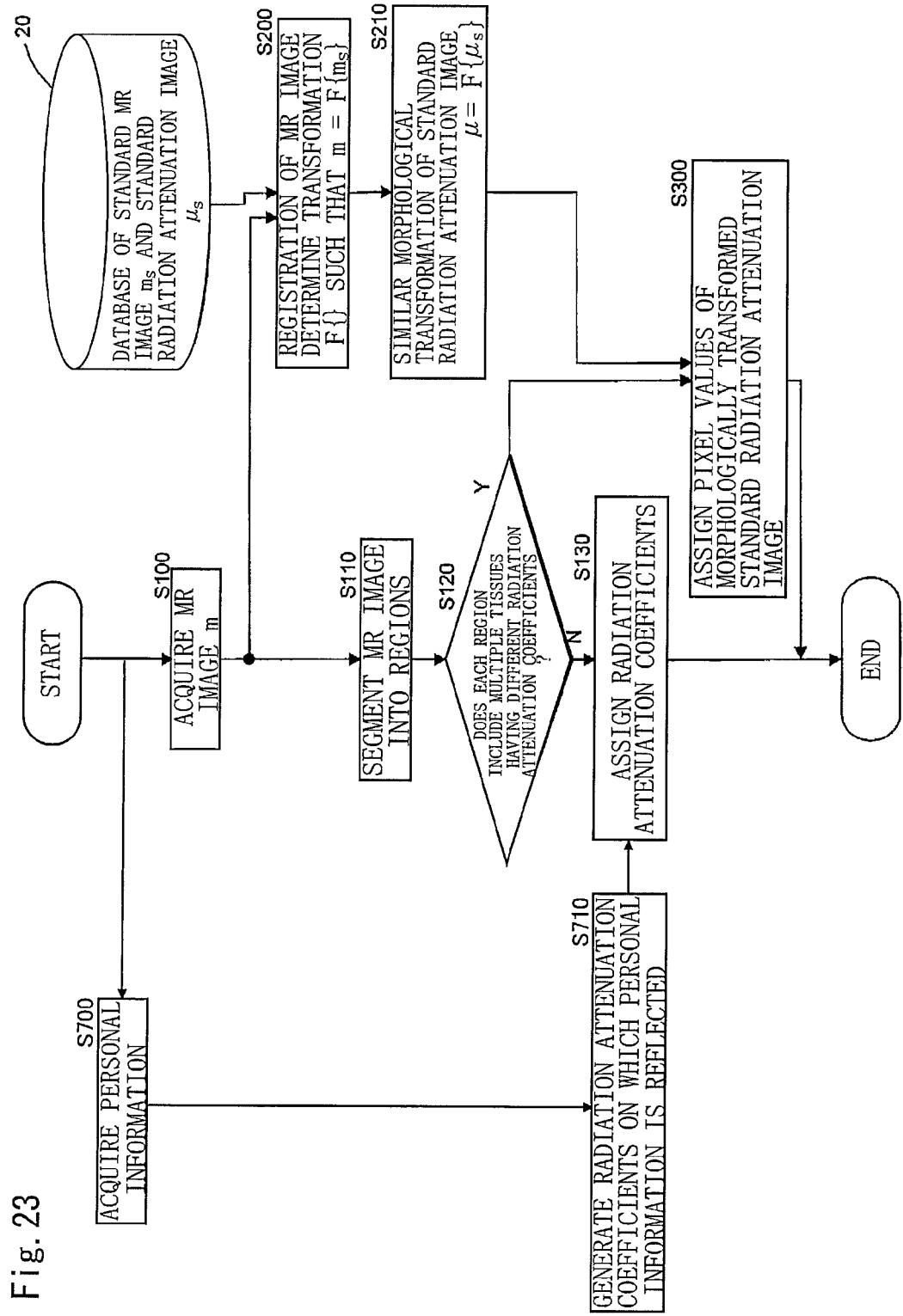
FIG. 23 is a flowchart showing a processing procedure according to a sixteenth embodiment of the present invention.
Figure 24:
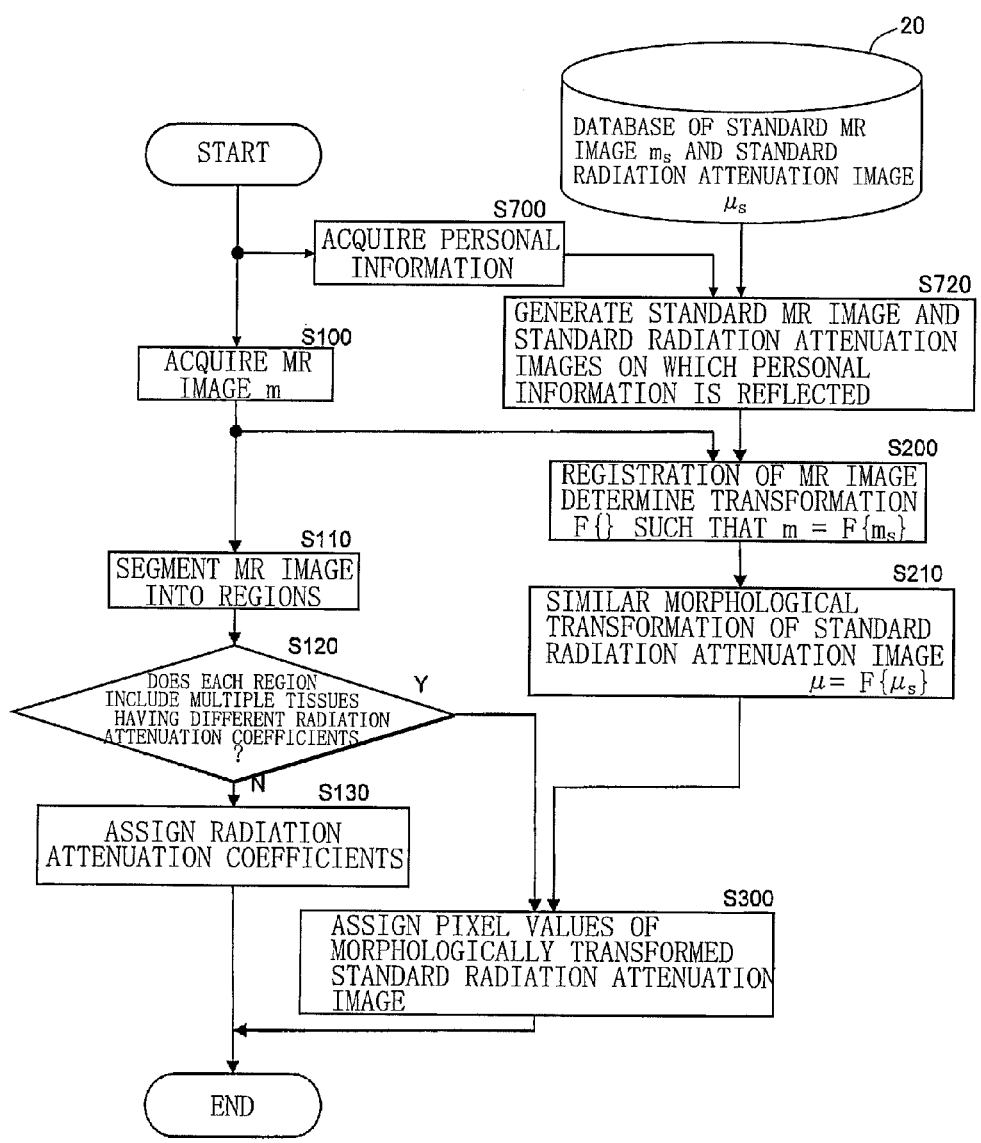
FIG. 24 is a flowchart showing a processing procedure according to a seventeenth embodiment of the present invention.

Moreover, as in a sixteenth embodiment shown in FIG. 23 and a seventeenth embodiment shown in FIG. 24, the standard image and/or the radiation attenuation coefficients can be customized on the basis of personal information about the subject (DNA, age, sex, height, weight, place of birth, place of residence, medical history, and the like) with a further improvement in accuracy. In FIGS. 23 and 24, S700 represents a step of acquiring personal information. S710 represents a step of generating radiation attenuation coefficients on which the personal information is reflected. S729 represents a step of generating a standard MR image and a standard radiation attenuation image on which the personal information is reflected. In other respects, the embodiments are the same as the first embodiment shown in FIG. 4. A description thereof is thus omitted.

Note that the standard image to be used with the standard MR image is not limited to the radiation attenuation image. Other embodiments are also applicable by the following translation according to the database. With the database 30 of the standard MR image and the standard CT image, S210 may be replaced with S520 and S530 of FIG. 13. With the database 40 of the standard MR image and the standard UTE image, S210 may be replaced with S524 and S534 of FIG. 20.

The subject's own radiation attenuation correction values or the radiation attenuation image, or the CT image or the UTE image may be repeatedly used as at least either one of the radiation attenuation correction value table and the standard image.

In the foregoing embodiments, the present invention is applied to brain images. However, the applications of the present invention are not limited thereto. The number of segmented regions is not limited to three, either, including a high intensity region, a medium intensity region, and a low intensity region.

INDUSTRIAL APPLICABILITY

The present invention is applicable to PET/MRI which combines PET with MRI.

The disclosure of the description, drawings, and claims of Japanese Patent Application No. 2007-074906, filed on Mar. 28, 2012, is incorporated herein by reference in its entirety.

REFERENCE SIGNS LIST

10 . . . subject
12 . . . radiation source
14 . . . detector
20 . . . database of standard MR image and standard radiation attenuation image
30 . . . database of standard MR image and standard CT image
40 . . . database of standard MR image and standard UTE image

The invention claimed is:
1. A method for generating an image for PET attenuation correction from an MR image, comprising:
    segmenting an MR image captured by MRI into regions according to pixel values,
    determining a radiation attenuation correction value in a region in which a radiation attenuation coefficient is considered to be uniform by referring to an existing radiation attenuation correction value table, and
    determining a radiation attenuation correction value in a region including multiple tissues having different radiation attenuation coefficients by referring to a standard image.
2. The method for generating an image for PET attenuation correction from an MR image according to claim 1, wherein the standard image is deformed to an MR image of a subject when the standard image is referred to.
3. The method for generating an image for PET attenuation correction from an MR image according to claim 2, wherein the standard image is referred to by using an image of whole body tissue or an image of some tissues of the body tissue.
4. The method for generating an image for PET attenuation correction from an MR image according to claim 1, wherein the standard image is an image for PET attenuation correction, a CT image, or a UTE image.
5. The method for generating an image for PET attenuation correction from an MR image according to claim 1, wherein the MR image and the standard image are adjusted to each other in resolution.
6. The method for generating an image for PET attenuation correction from an MR image according to claim 1, wherein at least either one of the radiation attenuation correction value table and the standard image is modified according to personal information about the subject.
7. The method for generating an image for PET attenuation correction from an MR image according to claim 1, wherein subject's own radiation attenuation correction values or the image for PET attenuation correction, or the CT image or the UTE image is repeatedly used as at least either one of the radiation attenuation correction value table and the standard image.
8. A non-transitory computer readable medium storing a program for causing a computer to execute the method as set forth in claim 1.

* * * * *

UNITED STATES PATENT AND TRADEMARK OFFICE
CERTIFICATE OF CORRECTION

PATENT NO.      : 9,342,903 B2
APPLICATION NO. : 14/385683
DATED           : May 17, 2016
INVENTOR(S)     : Taiga Yamaya et al.

Page 1 of 1

It is certified that error appears in the above-identified patent and that said Letters Patent is hereby corrected as shown below:

Title Page Item (72) Inventors: delete "Mikio Suga, Ichujawa (JP);" and add -- Mikio Suga, Ichikawa (JP); --, therefor.

Signed and Sealed this
Ninth Day of August, 2016

Michelle K. Lee
*Director of the United States Patent and Trademark Office*